(12) United States Patent
Riordan et al.

(10) Patent No.: US 7,695,923 B2
(45) Date of Patent: Apr. 13, 2010

(54) CFTR POLYPEPTIDES METHODS TO OVERCOME BIOSYNTHETIC MISPROCESSING

(75) Inventors: John R. Riordan, Scottsdale, AZ (US); Xiu-Bao Chang, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 326 days.

(21) Appl. No.: 11/565,551

(22) Filed: Nov. 30, 2006

(65) Prior Publication Data

US 2008/0020418 A1 Jan. 24, 2008

Related U.S. Application Data

(63) Continuation of application No. 10/030,585, filed as application No. PCT/US00/40324 on Jul. 7, 2000, now Pat. No. 7,205,272.

(60) Provisional application No. 60/143,090, filed on Jul. 9, 1999, provisional application No. 60/146,097, filed on Jul. 21, 1999.

(51) Int. Cl.
*G01N 33/53* (2006.01)
(52) U.S. Cl. ..................................................... 435/7.2
(58) Field of Classification Search ........................ None
See application file for complete search history.

(56) References Cited

U.S. PATENT DOCUMENTS

| 5,543,399 A | 8/1996 | Riordan et al. |
| 5,639,661 A | 6/1997 | Welsh et al. |
| 5,750,571 A | 5/1998 | Cheng et al. |
| 5,888,722 A | 3/1999 | Costa De Beauregard et al. |
| 5,900,360 A | 5/1999 | Welch et al. |

FOREIGN PATENT DOCUMENTS

| EP | 0 446 017 | 3/1991 |
| WO | WO 92/05252 | 4/1992 |
| WO | WO 92/05273 | 4/1992 |
| WO | WO 94/12649 | 6/1994 |
| WO | WO 95/25796 | 9/1995 |
| WO | WO 01/03722 | 1/2001 |

OTHER PUBLICATIONS

U.S. Appl. No. 07/488,307.
U.S. Appl. No. 07/589,295.
Chang et al., "Removal of Multiple Arginine-Framed Trafficking Signals Overcomes Misprocessing of ΔAF508 CFTR Present in Most Patients with Cystic Fibrosis," *Molec. Cell*, 1999, 4:137-42.
Meckle et al., "Genotype-phenotype relationships in cystic fibrosis," *Med. Clin. North Am.*, 2000, 84(3):597-607.
Voet et al., *Biochemistry*, 1990, John Wiley & Sons, Inc. pp. 126-128 and 228-234.
Yan et al., "Two-amino acid molecular switch in an epithelial morphogen that regulates binding to two distinct receptors," *Science*, 2000, 290:523-527.
Zerangue et al., "A New ER Trafficking Signal Regulates the Subunit Stoichiometry of Plasma Membrane KATP Channels," *Neuron*, 1999, 22:537-548.

*Primary Examiner*—Michael Pak
(74) *Attorney, Agent, or Firm*—Fish & Richardson P.C.

(57) ABSTRACT

The invention relates to biosynthetic maturation of cell surface polypeptides and, more specifically, to particular CFTR polypeptides which exhibit increased transport to the cell surface and tripeptide amino acid sequences that promote or enhance transport of export-incompetent CFTR to the cell surface.

2 Claims, 8 Drawing Sheets

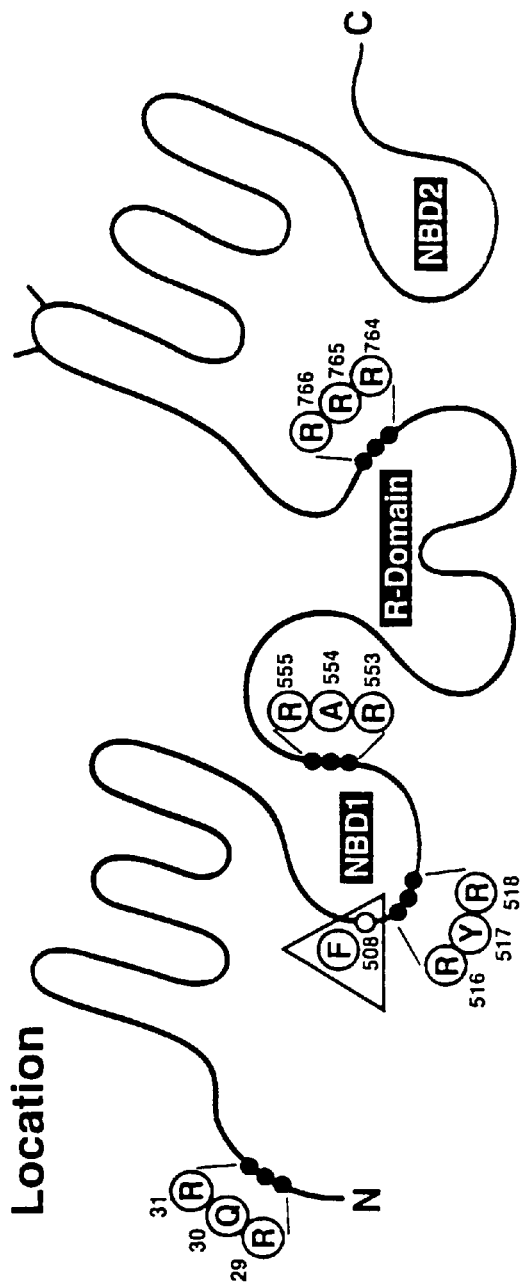

HUMAN CYSTIC FIBROSIS TRANSMEMBRANE CONDUCTANCE REGULATOR

```
   1 mqrsplekas vvsklffswt rpilrkgyrq rlelsdiyqi psvdsadnls eklerewdre
  61 laskknpkli nalrrcffwr fmfygiflyl gevtkavqpl llgriiasvd pdnkeersia
 121 iylgiglcll fivrtllllhp aifglhhigm qmriamfsli ykktlklssr vldkisigql
 181 vsllsnnlnk fdeglalahf vwiaplqval lmgiiwellq asafcglgfl ivialfqagl
 241 grmmmmkyrdq ragkiserlv itsemieniq svkayeweea mekmienlrq telkltrkaa
 301 yvryfnssaf ffsgffvvfl svlpyalikg iilrkiftti sfcivlrmav trqfpwavqt
 361 wydslgaink iqdflqkqey ktleynlttt evvmenvtaf weegfgelfe kakqnnnnrk
 421 tsngddslff snfsllgtpv lkdinfkier gqllavagst gagktsllmm imgeiepseg
 481 kikhsgrisf csqfswimpg tikeniifgv sydeyryrsv ikacqleedi skfaekdniv
 541 lgeggitlsg gqrarislar avykdadlyl ldspfgyldv ltekeifesc vcklmanktr
 601 ilvtskmehl kkadkililh egssyfygtf selqnlqpdf ssklmgcdsf dqfsaerrns
 661 iltetlhrfs legdapvswt etkkqsfkqt gefgekrkns ilnpinsirk fsivqktplq
 721 mngieedsde plerrlslvp dseqgeailp risvistgpt lqarrqsvl nlmthsvnqg
 781 qnihrkttas trkvslapqa nlteldiysr rlsqetglei seeineedlk ecffddmesi
 841 pavttwntyl ryitvhksli fvliwclvif laevaaslvv lwllgntplq dkgnsthsrn
 901 nsyaviitst ssyyvfyiyv gvadtllamg ffrglplvht litvskilhh kmlhsvlqap
 961 mstlntlkag gilnrfskdi ailddllplt ifdfiqllli vigaiavvav lqpyifvatv
1021 pvivafimlr ayflqtsqql kqlesegrsp ifthlvtslk glwtlrafgr qpyfetlfhk
1081 alnlhtanwf lylstlrwfq mriemifvif fiavtfisil ttgegegrvg iiltlamnim
1141 stlqwavnss idvdslmrsv srvfkfidmp tegkptkstk pykngqlskv miienshvkk
1201 ddiwpsggqm tvkdltakyt eggnaileni sfsispgqrv gllgrtgsgk stllsaflrl
1261 lntegeiqid gvswdsitlq qwrkafgvip qkvfifsgtf rknldpyeqw sdqeiwkvad
1321 evglrsvieq fpgkldfvlv dggcvlshgh kqlmclarsv lskakillld epsahldpvt
1381 yqiirrtlkq afadctvilc ehrieamlec qqflvieenk vrqydsiqkl lnersifrqa
1441 ispsdrvklf phrnsskcks kpqiaalkee teeevqdtrl
```

FIG. 6

SEQUENCE LISTING

<160> NUMBER OF SEQ ID NOS: 17

<210> SEQ ID NO 1
<211> LENGTH: 7
<212> TYPE: PRT
<213> ORGANISM: Homo sapiens

<400> SEQUENCE: 1

Gly Tyr Arg Gln Arg Leu Glu
 1               5

<210> SEQ ID NO 2
<211> LENGTH: 7
<212> TYPE: PRT
<213> ORGANISM: Homo sapiens

<400> SEQUENCE: 2

```
Glu Tyr Arg Tyr Arg Ser Val
 1               5
```

<210> SEQ ID NO 3
<211> LENGTH: 7
<212> TYPE: PRT
<213> ORGANISM: Homo sapiens

<400> SEQUENCE: 3

```
Gly Gln Arg Ala Arg Ile Ser
 1               5
```

<210> SEQ ID NO 4
<211> LENGTH: 7
<212> TYPE: PRT
<213> ORGANISM: Homo sapiens

<400> SEQUENCE: 4

```
Gln Ala Arg Arg Arg Gln Ser
 1               5
```

<210> SEQ ID NO 5
<211> LENGTH: 1480
<212> TYPE: PRT
<213> ORGANISM: Homo sapiens

<400> SEQUENCE: 5

```
Met Gln Arg Ser Pro Leu Glu Lys Ala Ser Val Val Ser Lys Leu Phe
 1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240
```

-continued

```
Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655
```

-continued

```
Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile Val
    1010                1015                1020

Ala Phe Ile Met Leu Arg Ala Tyr Phe Leu Gln Thr Ser Gln Gln Leu
1025                1030                1035                1040

Lys Gln Leu Glu Ser Glu Gly Arg Ser Pro Ile Phe Thr His Leu Val
                1045                1050                1055

Thr Ser Leu Lys Gly Leu Trp Thr Leu Arg Ala Phe Gly Arg Gln Pro
            1060                1065                1070
```

-continued

```
Tyr Phe Glu Thr Leu Phe His Lys Ala Leu Asn Leu His Thr Ala Asn
        1075                1080                1085
Trp Phe Leu Tyr Leu Ser Thr Leu Arg Trp Phe Gln Met Arg Ile Glu
        1090                1095                1100
Met Ile Phe Val Ile Phe Phe Ile Ala Val Thr Phe Ile Ser Ile Leu
1105                1110                1115                1120
Thr Thr Gly Glu Gly Glu Gly Arg Val Gly Ile Ile Leu Thr Leu Ala
                1125                1130                1135
Met Asn Ile Met Ser Thr Leu Gln Trp Ala Val Asn Ser Ser Ile Asp
                1140                1145                1150
Val Asp Ser Leu Met Arg Ser Val Ser Arg Val Phe Lys Phe Ile Asp
                1155                1160                1165
Met Pro Thr Glu Gly Lys Pro Thr Lys Ser Thr Lys Pro Tyr Lys Asn
        1170                1175                1180
Gly Gln Leu Ser Lys Val Met Ile Ile Glu Asn Ser His Val Lys Lys
1185                1190                1195                1200
Asp Asp Ile Trp Pro Ser Gly Gly Gln Met Thr Val Lys Asp Leu Thr
                1205                1210                1215
Ala Lys Tyr Thr Glu Gly Gly Asn Ala Ile Leu Glu Asn Ile Ser Phe
        1220                1225                1230
Ser Ile Ser Pro Gly Gln Arg Val Gly Leu Leu Gly Arg Thr Gly Ser
        1235                1240                1245
Gly Lys Ser Thr Leu Leu Ser Ala Phe Leu Arg Leu Leu Asn Thr Glu
1250                1255                1260
Gly Glu Ile Gln Ile Asp Gly Val Ser Trp Asp Ser Ile Thr Leu Gln
1265                1270                1275                1280
Gln Trp Arg Lys Ala Phe Gly Val Ile Pro Gln Lys Val Phe Ile Phe
                1285                1290                1295
Ser Gly Thr Phe Arg Lys Asn Leu Asp Pro Tyr Glu Gln Trp Ser Asp
                1300                1305                1310
Gln Glu Ile Trp Lys Val Ala Asp Glu Val Gly Leu Arg Ser Val Ile
        1315                1320                1325
Glu Gln Phe Pro Gly Lys Leu Asp Phe Val Leu Val Asp Gly Gly Cys
        1330                1335                1340
Val Leu Ser His Gly His Lys Gln Leu Met Cys Leu Ala Arg Ser Val
1345                1350                1355                1360
Leu Ser Lys Ala Lys Ile Leu Leu Leu Asp Glu Pro Ser Ala His Leu
                1365                1370                1375
Asp Pro Val Thr Tyr Gln Ile Ile Arg Arg Thr Leu Lys Gln Ala Phe
        1380                1385                1390
Ala Asp Cys Thr Val Ile Leu Cys Glu His Arg Ile Glu Ala Met Leu
        1395                1400                1405
Glu Cys Gln Gln Phe Leu Val Ile Glu Glu Asn Lys Val Arg Gln Tyr
1410                1415                1420
Asp Ser Ile Gln Lys Leu Leu Asn Glu Arg Ser Leu Phe Arg Gln Ala
1425                1430                1435                1440
Ile Ser Pro Ser Asp Arg Val Lys Leu Phe Pro His Arg Asn Ser Ser
                1445                1450                1455
Lys Cys Lys Ser Lys Pro Gln Ile Ala Ala Leu Lys Glu Glu Thr Glu
                1460                1465                1470
Glu Glu Val Gln Asp Thr Arg Leu
        1475                1480
```

```
<210> SEQ ID NO 6
<211> LENGTH: 25
<212> TYPE: PRT
<213> ORGANISM: Homo sapiens

<400> SEQUENCE: 6

Ser Trp Thr Arg Pro Ile Leu Arg Lys Gly Tyr Arg Gln Arg Leu Glu
1               5                   10                  15

Leu Ser Asp Ile Tyr Gln Ile Pro Ser
            20                  25

<210> SEQ ID NO 7
<211> LENGTH: 25
<212> TYPE: PRT
<213> ORGANISM: Homo sapiens

<400> SEQUENCE: 7

Asn Ile Ile Phe Gly Val Ser Tyr Asp Glu Tyr Arg Tyr Arg Ser Val
1               5                   10                  15

Ile Lys Ala Cys Gln Leu Glu Glu Asp
            20                  25

<210> SEQ ID NO 8
<211> LENGTH: 25
<212> TYPE: PRT
<213> ORGANISM: Homo sapiens

<400> SEQUENCE: 8

Gly Glu Gly Gly Ile Thr Leu Ser Gly Gly Gln Arg Ala Arg Ile Ser
1               5                   10                  15

Leu Ala Arg Ala Val Tyr Lys Asp Ala
            20                  25

<210> SEQ ID NO 9
<211> LENGTH: 25
<212> TYPE: PRT
<213> ORGANISM: Homo sapiens

<400> SEQUENCE: 9

Ser Val Ile Ser Thr Gly Pro Thr Leu Gln Ala Arg Arg Gln Ser
1               5                   10                  15

Val Leu Asn Leu Met Thr His Ser Val
            20                  25

<210> SEQ ID NO 10
<211> LENGTH: 42
<212> TYPE: DNA
<213> ORGANISM: Artificial Sequence
<220> FEATURE:
<223> OTHER INFORMATION: primer

<400> SEQUENCE: 10 caatttgag gaaaggatac aaacagcgcc tggaattgtc ag                     42

<210> SEQ ID NO 11
<211> LENGTH: 42
<212> TYPE: DNA
<213> ORGANISM: Artificial Sequence
<220> FEATURE:
<223> OTHER INFORMATION: primer

<400> SEQUENCE: 11
ctgacaattc caggcgctgt ttgtatcctt tcctcaaaat tg                    42
```

```
<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
cctatgatga atataaatac agaagcctca tc                                    32

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
gatgacgctt ctgtatttat attcatcata gg                                    32

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
ggaggtcaac gagcaaaaat ttctttagca agag                                  34

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
ctcttgctaa agaaattttt gctcgttgac ctcc                                  34

<210> SEQ ID NO 16
<211> LENGTH: 34
<212> TYPE: DNA
<213> ORGANISM: Artificial Sequence
<220> FEATURE:
<223> OTHER INFORMATION: primer

<400> SEQUENCE: 16
cttcaggcac gaaggaagca gtctctcctg aacc                                  34

<210> SEQ ID NO 17
<211> LENGTH: 33
<212> TYPE: DNA
<213> ORGANISM: Artificial Sequence
<220> FEATURE:
<223> OTHER INFORMATION: primer

<400> SEQUENCE: 17
ggttcaggac agactgcttc cttcgtgctg aag                                   33
```

CFTR POLYPEPTIDES METHODS TO OVERCOME BIOSYNTHETIC MISPROCESSING

CROSS-REFERENCE TO RELATED APPLICATIONS

This application is a continuation application of U.S. Ser. No. 10/030,585, filed Jan. 8, 2002, which is a National Stage application under 35 U.S.C. §371 and claims benefit under 35 U.S.C. §119(a) of International Application No. PCT/US00/40324, filed Jul. 7, 2000, which claims the benefit of U.S. Application Ser. No. 60/143,090, filed Jul. 9, 1999, and U.S. Application Ser. No. 60/146,097, filed Jul. 21, 1999. The disclosures of the prior applications are considered part of (and are incorporated by reference in) the disclosure of this application.

STATEMENT AS TO FEDERALLY SPONSORED RESEARCH

This invention was made with Government support under DK054076 and DK051870 awarded by the National Institutes of Health's National Institute of Diabetes and Digestive and Kidney Diseases. The Government has certain rights in the invention.

BACKGROUND OF THE INVENTION

The invention relates to biosynthetic maturation of cell surface polypeptides and, more specifically, to particular CFTR polypeptides which exhibit increased transport to the cell surface and tripeptide amino acid sequences that promote or enhance transport of export-incompetent CFTR to the cell surface.

Large multidomain and multisubunit proteins are assembled into their native tertiary and quaternary structures, respectively, in the endoplasmic reticulum (ER). If this assembly is imperfect because of mutations or for other reasons, the aberrant protein is targeted for degradation by a set of processes generally referred to as biosynthetic quality control. Although a great deal has been learned about these processes in the past few years the rate-limiting step determining whether or not a nascent chain is exported from the ER has not been identified. Indeed, the relation of the folding and degradation mechanisms to the ER export and retrieval pathways is not understood for any cell surface or secreted molecule.

Cystic fibrosis (CF) is an example of a disease which may benefit from an understanding of the factors that contribute to or mediate retention or export of proteins from the endoplasmic reticulum because, in many patients, ER-retention prevents potentially functional variant CFTR (Cystic Fibrosis Transmembrane Conductance Regulator) molecules from reaching the plasma membranes of secreting and reabsorbing epithelial cells, where CFTR is required as a regulated chloride channel. For example, although more than 800 different mutations in the CFTR gene have been detected in CF patients, more than 90% of patients possess a single misprocessing mutant, ΔF508. Collins, F. S. (1992) *Science* 256:774-779. This mutant protein is potentially functional as a regulated chloride channel if it can be made to move further along the secretory pathway and reach the cell surface. Dalemans, W. et al. (1991) *Nature* 354:526-528; Drumm, M. L. et al. (1991). *Science* 254:1797-1799; and Li, C. et al. (1993) *Nat. Genetics* 3:311-316.

Ubiquitination ultimately marks maturation-incompetent nascent chains as substrates for the proteasome but earlier steps in the recognition of these targets are unclear. Jensen, T. J. et al. (1995) *Cell* 83:129-135; Sato, S. et al. (1998). *J. Biol. Chem.* 273:7189-92; and Ward, C. L et al. (1995) *Cell* 83:121-127. Molecular chaperones can either retain unfolded proteins or assist in their folding. Nascent CFTR interacts with chaperones on both sides of the ER membrane; on the cytoplasmic face of the ER, Hsp70 (Yang, Y. et al. (1993) *Proc. Natl. Acad. Sci. USA* 90:9480-9484) and its cochaperone, Hdj-2 (Meacham, G. C. et al. (1999) *EMBO J.* 18:1492-1505) as well as Hsp90 (Loo et al. (1998) *EMBO J.* 17:6879-6887) bind to immature CFTR. Other chaperones could also be present in the large multimolecular complexes containing nascent CFTR. Pind, S. et al. (1994) *J. Biol. Chem.* 269:12784-12788. Although these interactions appear to occur with both wild-type CFTR and mutant ΔF508 CFTR and no large differences in the kinetics or stoichiometry of CFTR-chaperone interactions have yet been found, the role of chaperones in ER retention of CFTR cannot be ruled out.

In addition to chaperones, short sequence motifs have been shown to exert positive and negative effects on secretory proteins which are required for ER export and retrieval, respectively. For example, a short diacidic ER export signal has been described as necessary for transport of VSV-G glycoprotein from the ER. Nishimura, N., and Balch, W. E. (1997) *Science* 277:556-8. Whether nascent ΔF508 CFTR never leaves the ER or if it is retrieved is not known, although ΔF508 CFTR may reach the intermediate compartment (ER-GIC) between ER and Golgi. Gilbert, A. et al. (1998) *Exp. Cell Res.* 242:144-52.

Previous attempts to overcome ER-retention of mutant CFTR have included inhibition of the proteasome involved in nascent chain proteolysis (Jensen et al., 1995, supra; Ward et al., 1995, supra), perturbation of interaction with molecular chaperons (Jiang, C. et al. (1998). *Am. J. Physiol.* 275:C171-8; and Loo et al., 1998, supra) and using agents or conditions which influence protein folding for example, glycerol and other osmolytes (Brown, C. R. et al. (1996) *Cell Stress Chaperones* 1:117-25; Qu, B. H. et al. (1997) *J. Biol. Chem.* 272:15739-44; and Sato, S. et al. (1996) *J. Biol. Chem.* 271:635-638) or reduced temperature (Denning, G. M. et al. (1992) *Nature* 358:761-764). However, these treatments are minimally effective or extremely toxic to cells, precluding their application to patients.

Thus, there remains a need to understand the biological basis for ER retention, especially in respect to the retention of proteins such as CFTR that have severe physiological consequences. The present invention satisfies this need and provides related advantages as well.

SUMMARY OF THE INVENTION

The present invention is based on the discovery that an export-incompetent CFTR has several arginine-framed tripeptide sequence motifs that contribute to the observed deficiency of cell surface expression, and that modifying one or more of these sequences can result in increased transport of the export-incompetent CFTR to the cell surface. In one aspect, the invention features an isolated polypeptide that includes a polypeptide having the sequence X1-R-X2-R-X3, wherein X1, X2 and X3 are any amino acid and polynucleotides encoding such polypeptides. The polypeptide can have at least seven amino acids. The invention also features an isolated polypeptide selected from the group consisting of: GYRQRLE (SEQ ID NO:1), EYRYRSV (SEQ ID NO:2), GQRARIS (SEQ ID NO:3) and QARRRQS (SEQ ID NO:4), and polynucleotides encoding such polypeptides. Polypeptides of the invention further can include a pharmaceutical formulation.

The invention also features an isolated polypeptide having one or more R-X-R sequences, wherein at least one R of an R-X-R sequence has been substituted with another amino acid, and wherein the substituted polypeptide is exported from the ER in an amount or at a rate greater than the unsubstituted polypeptide. The polypeptide can be CFTR.

In another aspect, the invention features a method for identifying a therapeutic agent for treating cystic fibrosis. The method includes contacting at least one cell expressing an export-incompetent CFTR with a test agent under conditions allowing an interaction between the agent and a factor mediating or contributing to export-incompetence; and determining whether the agent increases the amount of the CFTR on the cell surface, where an increased amount of CFTR on the cell surface identifies a therapeutic agent for treating cystic fibrosis.

In yet another aspect, the invention features a method for identifying an agent that induces or increases transport of an export-incompetent protein. The method includes contacting an export-incompetent protein with a test agent under conditions allowing an interaction between the agent and a factor mediating or contributing to export-incompetence; and determining whether the agent increases the amount or the rate of protein transported, where an increased amount of transported protein identifies an agent that induces or increases transport of an export-incompetent protein. The protein can be a secreted protein, a cell surface protein, or CFTR. The method can be performed in vitro or the export-incompetent protein can be expressed in a cell.

The invention also features a method for treating a subject having cystic fibrosis. The method includes administering to the subject a pharmaceutical formulation comprising a polypeptide having an R-X-R sequence in an amount effective for treating cystic fibrosis. In one embodiment, the X amino acid of the R-X-R sequence is not alanine, asparagine or glutamate. The polypeptide can have at least four amino acids, e.g., at least seven amino acids. The polypeptide can be selected from the group consisting of: GYRQRLE (SEQ ID NO:1), EYRYRSV (SEQ ID NO:2), GQRARIS (SEQ ID NO:3) and QARRRQS (SEQ ID NO:4).

In yet another aspect, the invention features a method for treating a subject having cystic fibrosis. The method includes administering to the subject a pharmaceutical formulation that includes a nucleic acid encoding a polypeptide having an R-X-R sequence in an amount effective for treating cystic fibrosis.

In another aspect, the invention features a method for treating a subject having or suspected of having a physiological disorder associated with an export-incompetent protein. The method includes administering to the subject a pharmaceutical formulation comprising a polypeptide having an R-X-R sequence in an amount effective for treating a physiological disorder associated with an export-incompetent protein. The physiological disorder or condition can be selected from the group consisting of: macular dystrophy and Stargardt's disease. The export-incompetent protein can be selected from the group consisting of: ion channels, ABC proteins, growth factors, immune regulators, adhesion proteins, hormones, clotting factors, hemostatic regulators and receptors thereof. In one embodiment, the X amino acid of the R-X-R sequence is not alanine, asparagine or glutamate. The polypeptide can have at least four amino acids, e.g., at least seven amino acids. The polypeptide can be selected from the group consisting of: GYRQRLE (SEQ ID NO:1), EYRYRSV (SEQ ID NO:2), GQRARIS (SEQ ID NO:3) and QARRRQS (SEQ ID NO:4).

In yet another aspect, the invention features a method for inducing or increasing intracellular transport of an export-incompetent protein. The method includes contacting a cell expressing an export-incompetent protein with a composition comprising a polypeptide having an R-X-R sequence in an amount sufficient for inducing or enhancing intracellular transport of the export-incompetent protein. The protein can have an R-X-R sequence and can be a cell surface protein, an export-incompetent CFTR, or a secreted protein.

A method for identifying an agent that inhibits or disrupts an interaction between an R-X-R polypeptide and an ER retention factor also is described. The method includes incubating a polypeptide having an R-X-R sequence and an ER retention factor under conditions allowing their interaction; adding a test agent to the incubation; and detecting binding between the polypeptide and the ER retention factor, where decreased binding in the presence of the test agent identifies an agent that inhibits or disrupts an interaction between an R-X-R polypeptide and an ER retention factor. The method can be performed in vitro. The polypeptide can have at least 4 amino acids. The X amino acid of the R-X-R sequence may not be alanine, asparagine or glutamate. The polypeptide can be selected from the group consisting of: GYRQRLE (SEQ ID NO:1), EYRYRSV (SEQ ID NO:2), GQRARIS (SEQ ID NO:3) and QARRRQS (SEQ ID NO:4).

The invention also features a method for identifying an ER retention factor. The method includes contacting a composition suspected of containing an ER retention factor with a polypeptide having an R-X-R sequence under conditions allowing interaction between the factor and the polypeptide; and detecting binding between the factor and the polypeptide, thereby identifying an ER retention factor. The method can be performed in vitro. The polypeptide can have at least four amino acids, e.g., at least seven amino acids. The polypeptide can be selected from the group consisting of: GYRQRLE (SEQ ID NO:1), EYRYRSV (SEQ ID NO:2), GQRARIS (SEQ ID NO:3) and QARRRQS (SEQ ID NO:4).

In yet another aspect, the invention features a method for inhibiting degradation of a protein in a cell. The method includes contacting a cell with a polypeptide having an R-X-R sequence in an amount sufficient for inhibiting degradation of a cell surface or secreted protein. The protein can be a cell surface protein or a secreted protein.

A method for detecting the presence of an export-incompetent protein in a cell is also featured. The method includes contacting a cell with a polypeptide having an R-X-R sequence and detecting the intracellular transport of the protein. The intracellular transport can be detected using an enzyme, by detecting the presence of the protein on the cell surface, or by detecting secretion of the protein. The protein can be CFTR.

BRIEF DESCRIPTION OF THE DRAWINGS

FIGS. 1A to 1D show A) a schematic depiction of CFTR protein indicating approximate locations of arginine-framed tripeptide sequences and phenylalanine 508; B) western blots of wild-type and ΔF508 CFTR expressed in BHK cells having the indicated substitutions; C) wild-type and ΔF508 CFTR expressed in BHK cells having all four arginines substituted with lysine (ΔF508/4RK) digested with endoglycosidase H; and D) surface biotinylation of mature CFTR on cells expressing ΔF508, ΔF508/4RK and wild-type CFTR. The arrowhead indicates position of mature band with complex (endoH resistant) oligosaccharide chains. Solid arrows indicate the position of core-glycosylated band before endo-H digestion and open arrows are after endo-H digestion. Amino acid numbering begins from the first methionine in CFTR. Expression, extraction, digestion and cell surface labeling was performed as described in Example I.

FIG. 6 is an amino acid sequence of human cystic fibrosis transmembrane conductance regulator (CFTR) (SEQ ID NO:5).

DETAILED DESCRIPTION OF THE INVENTION

Figure 1C:
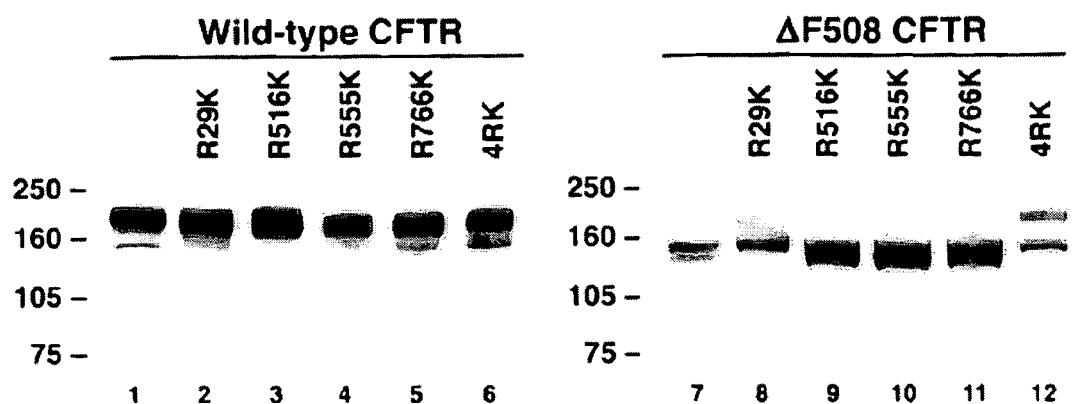

The present invention is based upon the discovery that particular mutant CFTR's are unable to be transported to the cell surface due, in part, to the presence of arginine-framed tripeptide sequence motifs, R-X-R, present in CFTR. There are four arginine-framed tripeptide sequence motifs on CFTR that appear to mediate or contribute to retention of mutant export-incompetent CFTR in the endoplasmic reticulum (ER), delaying or preventing transport of CFTR to the cell surface. When altered, such as by substituting one arginine of the tripeptide sequence motif with another amino acid, an increase in transport of the substituted CFTR to the cell surface in an amount greater than unsubstituted export-incompetent CFTR is observed. Thus, agents that induce or increase transport of export-incompetent CFTR or other export-incompetent proteins from the ER can be used as therapeutics for treating physiological diseases associated with export-incompetent proteins, such as cystic fibrosis (CF).

In one embodiment, the invention provides isolated CFTR polypeptides having one or more amino acid substitutions of an arginine-framed tripeptide (AFT). The substituted CFTR polypeptides are capable of being transported to the cell surface in an amount greater than an unsubstituted CFTR polypeptide. Thus, substituted CFTR polypeptides are useful for the treatment of CF, for example. Moreover, as AFTs can mediate or contribute to a protein's inability to be transported from the ER, AFT and peptide sequences containing such AFT sequences are useful as competitive inhibitors of ER retention factors that interact with AFT containing polypeptides. As disclosed herein, competitive inhibition using such peptides induces or enhances ER transport of proteins, including export-incompetent proteins containing an arginine-framed tripeptide sequence. Thus, arginine-framed tripeptides are useful for treating physiological disorders related to export-incompetent proteins, including cell surface as well as secreted proteins, such as CFTR. Thus, in another embodiment, the invention provides peptides having one or more arginine-framed tripeptide sequences, and methods of use.

As used herein, the terms "protein," "polypeptide" and "peptide" are used interchangeably to denote an amino acid polymer that comprises at least two amino acids covalently linked by an amide bond, regardless of length or post-translational modification (e.g., glycosylation, phosphorylation, lipidation, ubiquitination etc.). D- and L-amino acids, and mixtures thereof are included.

As used herein, the terms "isolated" or "substantially pure," when used as a modifier of invention CFTR polypeptides, fragments thereof, arginine-framed tripeptides and nucleic acids, means that they are produced by the hand of man and are separated from their native in vivo cellular environment. Generally, polypeptides and nucleic acids so separated are substantially free of other proteins, nucleic acids, lipids, carbohydrates or other materials with which they are naturally associated.

Typically, a polypeptide is substantially pure when it is at least 60%, by weight, free from the proteins and naturally-occurring molecules with which it is naturally associated. Preferably, the preparation is at least 75%, more preferably at least 90%, and most preferably at least 95%, by weight. Substantially pure CFTR polypeptide can be obtained, for example, by extraction from a natural source (e.g., an animal cell); by expression of a recombinant nucleic acid encoding a CFTR polypeptide; or by chemically synthesizing the protein. Purity can be measured by any appropriate method, e.g., polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

As disclosed herein, substitution of one or more amino acids of an AFT sequence with a different amino acid can increase transport of an export-incompetent polypeptide (see for example, Examples I to III). Thus, in another embodiment, the invention provides an isolated polypeptide containing at least one arginine-framed tripeptide, R-X-R, in which at least one R of the R-X-R tripeptide is substituted with an amino acid, and the substituted polypeptide is exported from the endoplasmic reticulum in an amount greater than the unsubstituted polypeptide. In one aspect, the first or third R is substituted or the X position amino acid is substituted. In another aspect, the first or third R is substituted with a lysine. The X position amino acid is not substituted with alanine, asparagine or glutamate.

Particular examples of isolated polypeptides so substituted include export incompetent ΔF508 CFTR, for example, R29K and R516K, in which the first arginine has been substituted with a lysine, R555K and R766K, in which the third arginine has been substituted with a lysine, and 4RK, in which all four substitutions are combined (FIG. 1B). Additional modifications of the CFTR sequence may influence ER-retention or export. For example, substitution of transport signals within the CFTR C-terminal extension residues (amino acid residues 1380-1480) also can increase ER export of an export-incompetent CFTR.

As used herein the term "substituted," when used as a modifier of a polypeptide containing at least one arginine-framed tripeptide (R-X-R), means that one or more amino acids of the R-X-R sequence or a sequence that flanks R-X-R, has been substituted with another amino acid. Preferred amino acid substitutions occur at the first or third arginines of the R-X-R motif. More preferred substitutions occur at the first arginine of the R-X-R motif. Generally, substitutions of the sequence flanking R-X-R will be within about 15 amino acids of the motif, preferably within 10 amino acids and more preferably within five amino acids. Multiple amino acid substitutions of R-X-R or a sequence that flanks R-X-R also are included.

As used herein, the terms "export-incompetent" or "export-incompetence," when used as a modifier of a protein, polypeptide or peptide, refers to a decrease or absence of intracellular transport from the endoplasmic reticulum (ER) to and through the golgi apparatus (cis, medial, trans) to an ultimate destination, such as the cell surface, to the lysosomes or endosomes, or secreted from the cell. A decrease either can occur in the rate of transport (e.g., a time delay in the appearance of a protein on the cell surface) or in the overall amount of protein transported to its ultimate destination, or a combination thereof. As disclosed herein, the rate or amount of intracellular transport of a protein can be determined by detecting the amount of protein present at the cell surface or present in organelles distal to the ER, such as the golgi (e.g., cell surface immunoprecipitations or cell immunocytochemistry using antibody specific for the protein, Examples I to III), for secreted proteins, detecting the amount in the media, or detecting protein transport through the various ER to golgi transport stages, for example, by assaying polypeptides for the presence of complex oligosaccharide chains added by glycosyl transferases present in the golgi. For example, as described in Example I and shown in FIGS. 1 and 2, pulse-chase studies revealed that wild type CFTR maturation begins within an hour (acquires complex oligosaccharide chains resistant to endoglycosidase H digestion, i.e., "endo H resistant chains"), whereas export-incompetent ΔF508 CFTR fails to mature even after two hours (does not acquire endoglycosidase H resistant chains; compare FIG. 2A to 2C). Additional methods, both in vivo and in vitro, are known in the art that can be used for detecting an increase or decrease in intracellular transport of a protein.

The isolated invention polypeptides having a substituted R of the R-X-R will generally be proteins that are naturally present in the intracellular transport apparatus during their maturation and are therefore normally present on the cell surface, in lysosomes or endosomes, or are secreted by the cell. Thus, such polypeptides include cell surface ion channels, growth factors, immune response regulators receptors (cytokines and growth factors including interleukins, interferons etc.), adhesion proteins (e.g., integrins and galectins), hormones, clotting factors, hemostatic effectors and receptors thereof. Nevertheless, other polypeptides that are not naturally present in the intracellular transport apparatus, but are modified so as to be present in the intracellular transport apparatus, such as by attaching an appropriate targeting signal, also are included, so long as substituted polypeptide, as set forth herein, is exported to the cell surface in an amount greater than the unsubstituted polypeptide.

Polypeptides containing at least one arginine-framed tripeptide (AFT) in which at least one of the arginines has been substituted with another amino acid include export-incompetent polypeptides as well as polypeptides for which no export deficiency is apparent (e.g., wild-type proteins). Both naturally occurring and non-naturally occurring substituted polypeptides are included. Specific examples of polypeptides that can be substituted are ΔF508 CFTR polypeptides in which an arginine residue at position 29, 516, 555, 766 has been substituted with lysine. Specific examples of polypeptides for which no export deficiency is apparent are wild-type CFTR's in which one or more arginines of the arginine-framed tripeptides have been substituted. For example, wild-type CFTR in which four arginines have been substituted with lysine (wild-type/4RK) appears to undergo more rapid maturation than unsubstituted wild-type CFTR (compare FIG. 2A to 2B). As with substituted export-incompetent CFTR, wild type CFTR polypeptides can have one or more substitutions of the arginine at the indicated positions, or have multiply substituted arginines, in any combination. Additional export-incompetent CFTR polypeptides are known in the art and are specifically included when substituted as set forth herein.

The invention further includes polypeptides having minor variations, additions or deletions to the amino acid sequence of the polypeptides disclosed herein so long as the modified polypeptide has substantially the same biological activity or function as the unmodified polypeptide. As used herein, the term "substantially the same biological activity or function," when used in reference to a modified polypeptide, means that the polypeptide retains sufficient biological activity associated with the unmodified polypeptide as described herein or known in the art to provide normal tissue function.

Modified polypeptides are therefore distinct from substituted polypeptides because modified polypeptides can have modifications throughout the polypeptide that do not destroy biological activity, whereas substituted polypeptides have one or more amino acids of the R-X-R sequence or a flanking sequence substituted with another amino acid, where the substituted polypeptide is exported to the cell surface in an amount or at a rate greater than the unsubstituted polypeptide. Thus, a substituted polypeptide as set forth herein can be modified so long as the polypeptide is exported from the ER in an amount or at a rate greater than the unsubstituted polypeptide. For example, a substituted export-incompetent CFTR polypeptide having modifications would be exported from the ER in an amount or at a rate greater than unsubstituted export-incompetent CFTR. Similarly, a substituted wild-type CFTR having modifications would be exported to the cell surface in an amount greater than unsubstituted wild-type CFTR.

Modified polypeptides that are "biologically active" or "functional" can be identified through a functional assay. For example, modified CFTR will exhibit substantial chloride efflux. An example of a functional assay for a polypeptide having an AFT, would be the ability of the modified AFT to induce or increase transport of an export incompetent protein. Additional functional assays for CFTR are known in the art and various assays for determining whether a modified polypeptide, such as a cell surface or secreted protein, has a biological function or activity include ion transport, ligand binding, cell signaling, the ability to bind or interact with proteins in vitro or in vivo, enzymatic activity, gene activation or suppression and the ability to be modulated by agents or proteins, for example.

As modified polypeptides will retain biological activity associated with unmodified polypeptide, modified polypeptides will generally have an amino acid sequence "substantially identical" to the amino acid sequence of the unmodified polypeptide. As used herein, the term "substantially identical," when used in reference to a polypeptide, means that a sequence of the polypeptide is at least 50% identical to a reference sequence. Modified polypeptides and substantially identical polypeptides will have at least 70%, preferably 88%, more preferably 90%, and most preferably 95% homology to a reference polypeptide. For polypeptides, the length of comparison between sequences will generally be at least 15 amino acids, preferably at least 25 amino acids, more preferably at least 50 amino acids, and most preferably 100 amino acids or more.

As used herein, the terms "homology" or "homologous," when used in reference to polypeptides, refers to the amino acid sequence similarity between two polypeptides. When an amino acid position in both of the polypeptides is occupied by identical amino acids, then they are homologous at that position. Thus, by "substantially homologous" is meant an amino acid sequence that is largely, but not entirely, homologous, and which retains most or all of the activity as the sequence to which it is homologous.

Modified or substantially identical polypeptides can have one or more additions, deletions, or insertions, or non-conservative variations, located at positions of the amino acid sequence which do not destroy the function of the protein (as determined by functional assays, e.g., as described herein) or conservative variations, for example, one amino acid can be substituted for another of the same class (e.g., valine for glycine, arginine for lysine, etc.).

An example of an addition is a heterologous domain that imparts a distinct functionality upon the polypeptide. A heterologous domain can be any small molecule, macromolecule or microfabricated device so long as it imparts an additional function. Particular heterologous domains include those that provide a targeting function (e.g., an antibody, ligand, viral envelope protein), those that enhance or suppress activity (a derepressible or activatable moiety), and those that enable purification (e.g., T7 tag, polyhistidine sequence etc.). The skilled artisan will know of other heterologous domains depending on the application and the distinct function desired.

An example of a deletion is where a small portion of the molecule is removed. For example, deletion of an AFT may not alter CFTR biological activity, but may induce or increase transport from the ER. Multiple deletions of AFTs may provide an additive or synergistic effect. Polypeptides having AFT deletions are specifically included so long as the deleted polypeptide has increased transport in comparison to undeleted polypeptide.

As used herein, the term "conservative variation" denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Modified polypeptides further include "chemical derivatives," in which one or more of the amino acids therein has a side chain chemically altered or derivatized. Such derivatized polypeptides include, for example, amino acids in which free amino groups form amine hydrochlorides, p-toluene sulfonyl groups, carobenzoxy groups; the free carboxy groups form salts, methyl and ethyl esters; free hydroxyl groups that form O-acyl or O-alkyl derivatives as well as naturally occurring amino acid derivatives, for example, 4-hydroxyproline for proline, 5-hydroxylysine for lysine, homoserine for serine, ornithine for lysine etc. Also included are D-amino acids and amino acid derivatives that can alter covalent bonding, for example, the disulfide linkage that forms between two cysteine residues that produces a cyclized polypeptide.

The polypeptide modifications may be deliberate, as by site-directed (e.g., PCR based) or random mutagenesis (e.g., EMS) or may be spontaneous or naturally occurring. For example, naturally occurring allelic or splice variants can arise by alternative RNA splicing, polymorphisms or spontaneous mutations of a nucleic acid. Further, deletion of one or more amino acids can also result in a modification of the structure of the resultant polypeptide without significantly altering a biological activity. Deletion can lead to the development of a smaller active molecule that may have broader utility. Those of skill in the art will recognize the numerous amino acids that can be modified or substituted with other chemically similar residues without substantially altering biological activity. All of the polypeptides produced by such modifications are included herein as long as the modified polypeptide possesses most or all of a biological activity or function as described herein.

As the AFT's of CFTR are disclosed herein as contributing to ER retention or delay in maturation of proteins, the AFT sequences are useful as competitive inhibitors of ER retention. Thus, in another embodiment, the present invention provides isolated polypeptides having an AFT sequence. The amino acid length of polypeptides that contain the AFT can range from about 4 amino acids up to about 50 amino acids. Preferably, the amino acid length is from about 5 to about 40 amino acids, more preferably, from about 6 to about 30 amino acids and, most preferably, from about 7 to about 25 amino acids. For example, the polypeptide can have the sequence $X_1$-R-$X_2$-R-$X_3$ where $X_1$, $X_2$ and $X_3$ are any amino acid. In certain aspects, the $X_2$ amino acid is not alanine, asparagine or glutamate.

Exemplary polypeptides having an AFT sequence are heptamers based on the AFT sequence region of the corresponding CFTR polypeptide. In particular, GYRQRLE (SEQ ID NO:1), which is based on the sequence SWTRPILRKGY-RQRLELSDIYQIPS (SEQ ID NO:6); EYRYRSV (SEQ ID NO:2), which is based on the sequence NIIFGVSYDEY-RYRSVIKACQLEED (SEQ ID NO:7); GQRARIS (SEQ ID NO:3), which is based on the sequence GEGGITLSG-GQRARISLARAVYKDA (SEQ ID NO:8); and QARRRQS (SEQ ID NO:4), which is based on the sequence SVIST-GPTLQARRRQSVLNLMTHSV (SEQ ID NO:9). It is understood that the standard single letter amino acid abbreviation is used to denote the amino acids of the invention polypeptides (see for example, Zubay, G. L., *Biochemistry* page 12, Addison-Wesely Publishing, Inc., 1983).

AFT containing polypeptides can have multiple AFT sequences, if desired. AFT polypeptides of the invention also can be modified as set forth herein so long as a biological activity or function is substantially the same as unmodified polypeptide. Additional modifications further include, for example, those that enhance or increase activity, so as to be more effective inhibitors of ER retention.

The polypeptides of the invention can be prepared by a variety of methods known in the art, such as by purification from an appropriate organism or cell using typical biochemical methods (e.g., column chromatography), by chemical synthesis (peptide synthesizers, e.g. Applied Biosystems, Inc., Model 540A (Foster City, Calif.)), by expression screening (using an antibody that binds to the polypeptide). An example of one means is by expression of a nucleic acid in a cell encoding an invention polypeptide in a host cell, such as bacteria, yeast or mammalian cell, and purifying the expressed polypeptide using methods known in the art. Other well known methods are described in Deutscher et al., (*Guide to Protein Purification: Methods in Enzymology* Vol. 182, Academic Press (1990)).

The invention further provides isolated nucleic acids encoding invention polypeptides, fragments thereof, complementary sequences thereto, and antisense sequences thereof. In one embodiment, invention isolated nucleic acids encode export incompetent CFTR's in which an R of the R-X-R motif is substituted, for example, with lysine. In another embodiment, invention isolated nucleic acids encode wild-type CFTR's in which an R of the R-X-R motif is substituted, for example, with lysine. In certain other aspects, nucleic acids encoding polypeptides having an AFT sequence also are provided.

As used herein, the terms "nucleic acid," "polynucleotide," "oligonucleotide," or "primer" are used interchangeably to refer to deoxyribonucleic acid (DNA) or ribonucleic (RNA), either double or single stranded, linear or circular. RNA can be unspliced or spliced mRNA, rRNA, tRNA or antisense RNA. DNA can be complementary DNA (cDNA), genomic DNA, or an antisense. Specially included are nucleotide analogues and derivatives, such as those used to provide resistance to degradation by nucleases, which can function as antisense or encode invention polypeptides.

An "isolated" or "substantially pure" nucleic acid means that the nucleic acid is not immediately contiguous with the coding sequences with either the 5' end or the 3' end with which it is immediately contiguous in the naturally occurring genome of the organism from which it is derived. The term therefore includes, for example, a recombinant DNA that is a separate molecule independent of other sequences (e.g., a cDNA or a genomic DNA fragment produced by PCR or restriction endonuclease treatment) as well as a recombinant DNA incorporated into a vector, an autonomously replicating plasmid or virus; or a genomic DNA of a prokaryote or eukaryote. It also includes a recombinant DNA that is part of a hybrid or fusion, for example, a gene encoding an additional polypeptide sequence. The term therefore does not include nucleic acids present among millions of sequences in a genomic or cDNA library, or in a restriction digest of a library fractionated on a gel.

The nucleic acids of the invention also include nucleic acids that are degenerate as a result of the genetic code. There are 20 natural amino acids, most of which are specified by more than one codon. Degenerate sequences may not selectively hybridize to other invention nucleic acids; however, they are nonetheless included as they encode invention polypeptides, arginine-framed tripeptide repeats and fragments thereof.

The invention also includes nucleic acids substantially homologous with the nucleic acids encoding invention polypeptides. As used herein, the term "homologous," when used in reference to nucleic acid molecule, refers to similarity between two nucleotide sequences. When a nucleotide position in both of the DNA molecules is occupied by identical nucleotides, then they are homologous at that position. Preferably, "substantially homologous" nucleic acid sequences are at least 70% homologous, more preferably at least 80% homologous and most preferably 90% homologous, and retains the biological activity associated with the sequence to which it is homologous. For nucleic acids, the length of comparison between sequences will generally be at least 30 nucleotides, preferably at least 50 nucleotides, more preferably at least 75 nucleotides, and most preferably 110 nucleotides or more. Algorithms for identifying homologous sequences that account for sequence gaps, mismatches, their length and location, are known in the art, such as BLAST (see e.g., Altschul et al, *J. Mol. Biol.* 215:403-10, 1990).

The invention nucleic acids are useful for encoding invention polypeptides, when such nucleic acids are incorporated into expression systems disclosed herein or known in the art. In addition, invention nucleic acids are useful as probes which can be used to identify the presence of a nucleic acid related to an invention nucleic acid or to detect the presence or an amount of DNA or mRNA in a sample, for example (Sambrook et al., *Molecular Cloning: A Laboratory Manual*, Cold Spring Harbor Laboratory, New York, 1989). Such probes can be modified so as to be detectable using radionuclides, luminescent moieties etc.

The invention further includes nucleic acid sequences complementary to the sequences described herein, such as antisense. Such single or double stranded RNA sequences (known as "RNA") are useful for inhibiting gene expression, for example (Kennerdell et al. (1998) *Cell* 95:1017-1026; Fire et al. (1998) *Nature* 391:806-811). Antisense sequences can interfere with a nucleic acid encoding a factor that mediates or contributes to ER retention (e.g., chaperones such as calnexin, hsc70 etc.). An effective amount of an antisense from the coding region of a factor that mediates or contributes to ER retention can be useful for treating physiological disorders associated with export-incompetent proteins including CFTR, as described herein.

Invention nucleic acid sequences can be obtained using various standard techniques known in the art (e.g., molecular cloning, chemical synthesis) and the purity can be determined by polyacrylamide or agarose gel electrophoresis, DNA sequencing and the like. Nucleic acids also can be isolated using hybridization or computer-based techniques, which are well known in the art. Such techniques include, but are not limited to: 1) hybridization of genomic DNA or cDNA libraries with probes to detect homologous nucleotide sequences; 2) antibody screening of polypeptides expressed by DNA sequences (e.g., using an expression library); 3) polymerase chain reaction (PCR) of genomic DNA or cDNA using primers capable of annealing to a nucleic acid sequence of interest; 4) computer searches of sequence databases for related sequences; and 5) differential screening of a subtracted nucleic acid library.

The nucleic acids of the invention can, if desired, be naked or be in a carrier suitable for passing through a cell membrane (e.g., DNA-liposome complex), contained in a vector (e.g., retroviral vector, adenoviral vectors and the like), or linked to inert beads or other heterologous domains (e.g., antibodies, biotin, streptavidin, lectins, etc.), or other appropriate compositions disclosed herein. Thus, both viral and non-viral means of nucleic acid delivery can be achieved and are contemplated. The nucleic acids of the invention also can contain additional nucleic acid sequences linked thereto that encodes a polypeptide having a distinct functionality, such as the heterologous domains set forth herein. Invention polynucleotides also can be modified, for example, to be resistant to nucleases to enhance their stability in a pharmaceutical formulation, for example.

For propagation or expression in cells, invention nucleic acids can be inserted into a vector. The term "vector" refers to a plasmid, virus or other vehicle known in the art that can be manipulated by insertion or incorporation of a nucleic acid.

Such vectors can be used for genetic manipulation (i.e., "cloning vectors") or can be used to transcribe or translate the inserted polynucleotide (i.e., "expression vectors"). A vector generally contains at least an origin of replication for propagation in a cell and a promoter. Control elements, including promoters, present within an expression vector are included to facilitate proper transcription and translation (e.g., splicing signal for introns, maintenance of the correct reading frame of the gene to permit in-frame translation of mRNA and, stop codons etc.).

In vivo or in vitro expression of the invention nucleic acids can be conferred by a promoter operably linked to the nucleic acid. "Promoter" refers to a minimal nucleic acid sequence sufficient to direct transcription of the nucleic acid to which the promoter is operably linked (see e.g., Bitter et al., *Methods in Enzymology* 153:516-544, 1987). Promoters can constitutively direct transcription, can be tissue-specific, or can render inducible or repressible transcription; such elements are generally located in the 5' or 3' regions of the native gene.

A "tissue-specific promoter" means a promoter that is active in particular cells or tissues which therefore confers transcription of the operably linked nucleic acid in the particular cells, e.g., liver cells, hematopoietic cells, or cells of a specific tissue within an animal, e.g., pancreatic β cells. The term also covers so-called "leaky" promoters, which regulate expression of a selected DNA primarily in one tissue, but cause expression in other tissues as well. An "inducible promotor" means a promoter whose activity level increases in response to treatment with an external signal or agent (e.g., metallothionein IIA promoter, heat shock promoter). A "repressible promotor" or "conditional promoter" means a promoter whose activity level decreases in response to a repressor or an equivalent compound. When the repressor is no longer present, transcription is activated or derepressed. Such promoters may be used in combination and also may include additional DNA sequences that are necessary for transcription and expression, such as introns and enhancer sequences.

As used herein, the term "operably linked" means that a selected nucleic acid (e.g., encoding a substituted export-incompetent CFTR) and a regulatory sequence(s) are connected in such a way as to permit transcription when the appropriate molecules (e.g., transcriptional activator proteins) are bound to the regulatory sequence(s). Typically, a promoter is in close proximity and 5' of the nucleic acid to allow the promoter to regulate expression of the nucleic acid. However, indirect operable linkage is also possible when a promoter on a first plasmid controls expression of a protein that, in turn, regulates a promoter controlling expression of the nucleic acid on a second plasmid.

When cloning in bacterial systems, constitutive promoters such as T7 and the like, as well as inducible promoters such as pL of bacteriophage λ, plac, ptrp, ptac (ptrp-lac hybrid promoter) may be used. When cloning in mammalian cell systems, constitutive promoters such as SV40, RSV and the like, or inducible promoters derived from the genome of mammalian cells (e.g., metallothionein promoter) or from mammalian viruses (e.g., the mouse mammary tumor virus long terminal repeat, the adenovirus late promoter) may be used. Promoters produced by recombinant DNA or synthetic techniques may also be used to provide for transcription of the nucleic acid sequences of the invention.

Mammalian expression systems which utilize recombinant viruses or viral elements to direct expression may be engineered. For example, when using adenovirus expression vectors, the nucleic acid sequence may be ligated to an adenovirus transcription/translation control complex, e.g., the late promoter and tripartite leader sequence. Alternatively, the vaccinia virus 7.5K promoter may be used. (see e.g., Mackett et al. (1982) *Proc. Natl. Acad. Sci. USA* 79:7415-7419; Mackett et al. (1984) *J. Virol.* 49:857-864; and Panicali et al. (1982) Proc. Natl. Acad. Sci. USA 79:4927-4931).

Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO92/05266 and WO92/14829). Vectors based on bovine papilloma virus (BPV) have the ability to replicate as extrachromosomal elements (Sarver et al., (1981) *Mol. Cell. Biol.* 1:486). Shortly after entry of an extrachromosomal vector into mouse cells, the vector replicates to about 100 to 200 copies per cell. Because transcription of the inserted cDNA does not require integration of the plasmid into the host's chromosome, a high level of expression occurs. Such vectors also have been employed in gene therapy (U.S. Pat. No. 5,719,054). CMV based vectors also are included (U.S. Pat. No. 5,561,063).

In yeast, a number of vectors containing constitutive or inducible promoters may be used (see e.g., *Current Protocols in Molecular Biology*, Vol. 2, Ch. 13, Ed. Ausubel et al., Greene Publish. Assoc. & Wiley Interscience, 1988; Grant et al., "Expression and Secretion Vectors for Yeast," in *Methods in Enzymology*, Vol. 153, pp. 516-544, Eds. Wu & Grossman, 31987, Acad. Press, N.Y., 1987; Glover, *DNA Cloning*, Vol. II, Ch. 3, IRL Press, Wash., D.C., 1986; Bitter, "Heterologous Gene Expression in Yeast," *Methods in Enzymology*, Vol. 152, pp. 673-684, Eds. Berger & Kimmel, Acad. Press, New York, 1987; and *The Molecular Biology of the Yeast Saccharomyces*, Eds. Strathern et al., Cold Spring Harbor Press, Vols. I and II, 1982). A constitutive yeast promoter such as ADH or LEU2 or an inducible promoter such as GAL may be used ("Cloning in Yeast," R. Rothstein In: *DNA Cloning, A Practical Approach*, Vol. 11, Ch. 3, Ed. D. M. Glover, IRL Press, Wash., D.C., 1986). Alternatively, vectors that facilitate integration of foreign nucleic acid sequences into a yeast chromosome, via homologous recombination for example, are known in the art and can be used. Yeast artificial chromosomes (YAC) are typically used when the inserted polynucleotides are too large for more conventional yeast expression vectors (e.g., greater than about 12 kb).

Thus, in accordance with the present invention, nucleic acids encoding invention polypeptides may be inserted into an expression vector for expression in vitro (e.g., using in vitro transcription/translation kits, which are available commercially), or may be inserted into an expression vector that contains a promoter sequence which facilitates transcription in either prokaryotes or eukaryotes by transfer of an appropriate nucleic acid into a suitable cell, organ, tissue or organism.

As used herein, a "transgene" is any piece of nucleic acid that is inserted by artifice into a host cell, and becomes part of the organism that develops from that cell. A transgene can include one or more promoters and any other DNA, such as introns, necessary for expression of the selected DNA, all operably linked to the selected DNA, and may include an enhancer sequence. A transgene may include a gene that is partly or entirely heterologous (i.e., foreign) to the transgenic organism, or may represent a gene homologous to an endogenous gene of the organism. Transgenes may integrate into the host cells genome or be maintained as a self-replicating plasmid (e.g., yeast 2μ plasmids).

As used herein, a "host cell" is a cell into which a nucleic acid is introduced that can be propagated, transcribed, or encoded polypeptide expressed. The term also includes any progeny of the subject host cell. It is understood that all progeny may not be identical to the parental cell since there may be mutations that occur during replication.

Host cells include but are not limited to microorganisms such as bacteria, yeast, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression.

For long-term expression of invention polypeptides, stable expression is preferred. Thus, using expression vectors that contain viral origins of replication, for example, cells can be transformed with a nucleic acid controlled by appropriate control elements (e.g., promoter/enhancer sequences, transcription terminators, polyadenylation sites, etc.). Although not wishing to be bound or so limited by any particular theory, stable maintenance of expression vectors in mammalian cells is believed to occur by integration of the vector into a chromosome of the host cell. Optionally, the expression vector also can contain a nucleic acid encoding a selectable or identifiable marker conferring resistance to a selective pressure thereby allowing cells having the vector to be identified, grown and expanded. Alternatively, the selectable marker can be on a second vector that is cotransfected into a host cell with a first vector containing an invention polynucleotide.

A number of selection systems may be used, including, but not limited to the herpes simplex virus thymidine kinase gene (Wigler et al. (1977) *Cell* 11:223), hypoxanthine-guanine phosphoribosyltransferase gene (Szybalska et al., *Proc. Natl. Acad. Sci. USA* 48:2026, 1962), and the adenine phosphoribosyltransferase (Lowy et al., *Cell* 22:817, 1980) genes can be employed in tk–, hgprt– or aprt– cells respectively. Additionally, antimetabolite resistance can be used as the basis of selection for dhfr, which confers resistance to methotrexate (Wigler et al. (1980) *Proc. Natl. Acad. Sci. USA* 77:3567; O'Hare et al. (1981) *Proc. Natl. Acad. Sci. USA* 78:1527); the gpt gene, which confers resistance to mycophenolic acid (Mulligan et al. (1981) *Proc. Natl. Acad. Sci. USA* 78:2072; the neomycin gene, which confers resistance to the aminoglycoside G-418 (Colberre-Garapin et al. (1981) *J. Mol. Biol.* 150:1); and the hygromycin gene, which confers resistance to hygromycin (Santerre et al. (1984) *Gene* 30:147). Recently, additional selectable genes have been described, namely trpB, which allows cells to utilize indole in place of tryptophan; hisD, which allows cells to utilize histinol in place of histidine (Hartman et al. (1988) *Proc. Natl. Acad. Sci. USA* 85:8047); and ODC (ornithine decarboxylase) which confers resistance to the ornithine decarboxylase inhibitor, 2-(difluoromethyl)-DL-ornithine, DFMO (McConlogue, In: *Current Communications in Molecular Biology*, Cold Spring Harbor Laboratory, ed., 1987).

As used herein, the term "transformation" means a genetic change in a cell following incorporation of DNA (e.g., a transgene) exogenous to the cell. Thus, a "transformed cell" is a cell into which, or a progeny of which, a DNA molecule has been introduced by means of recombinant DNA techniques.

Transformation of a host cell with DNA may be carried out by conventional techniques known to those skilled in the art. For example, when the host cell is a eukaryote, methods of DNA transformation include, for example, calcium phosphate co-precipitates, conventional mechanical procedures such as microinjection, electroporation, insertion of a plasmid encased in liposomes, and viral vectors. Eukaryotic cells also can be cotransformed with invention nucleic acid sequences or fragments thereof, and a second DNA molecule encoding a selectable phenotype, as those described herein. Another method is to use a eukaryotic viral vector, such as simian virus 40 (SV40) or bovine papilloma virus, to transiently infect or transform eukaryotic cells and express the protein (see e.g., *Eukaryotic Viral Vectors*, Cold Spring Harbor Laboratory, Gluzman ed., 1982). When the host is prokaryotic (e.g., *E. coli*), competent cells which are capable of DNA uptake can be prepared from cells harvested after exponential growth phase and subsequently treated by the $CaCl_2$ method using procedures well known in the art. Transformation of prokaryotes also can be performed by protoplast fusion of the host cell.

In another embodiment, the invention provides non-human transgenic animals having invention nucleic acids. As used herein, the term "animal," when modified by the term "transgenic," refers to an organism that reproduces sexually. Transgenic animals can be produced by methods known in the art.

The term "transgenic animal" refers to any animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated as described herein. In the present context, a "transgenic animal" does not encompass animals produced by classical crossbreeding or in vitro fertilization, but rather denotes animals in which one or more cells receive a recombinant DNA molecule. Invention transgenic animals can be either heterozygous or homozygous with respect to the transgene. Methods for producing transgenic animals are well known in the art (see for example, U.S. Pat. Nos. 5,721,367; 5,695,977; 5,650,298 and 5,614,396).

Preferred transgenic animals contain the transgene integrated into germ cells. Transgenic animals having a transgene integrated into germ cells have the ability to transfer the transgene to offspring. If such offspring in fact possess some or all of the transgene, then they, too, are transgenic animals. Homologous recombination is one mechanism in which a transgene is stably inserted into the genome. Although it is further preferred that the transgene be integrated into the animal's chromosome, the present invention also contemplates the use of extrachromosomally replicating sequences containing a transgene, such as those similar to yeast artificial chromosomes.

In the transgenic animals described herein, the transgene encodes a substituted polypeptide, such as CFTR, for example, or a peptide having an AFT sequence. A particularly useful transgenic would be an animal that exhibits characteristics of cystic fibrosis (e.g., that expresses an export-incompetent CFTR) which has been transformed with a transgene encoding a substituted CFTR or a polypeptide having an AFT sequence. Expression of the transgene can cause animal cells, such as air passageway epithelial cells or pancreatic cells, to increase CFTR expression on the cell surface. Animals that express other export-incompetent polypeptides can be transformed with a polypeptide having an AFT sequence, which can induce or increase intracellular transport of the export-incompetent cell surface polypeptide or secreted polypeptide. Alternatively, transgenic animals transformed with an antisense nucleic acid capable of inhibiting translation of an ER retention factor can exhibit increased export of export-incompetent or other proteins that utilize the intracellular transport pathway. Any animal that can be produced by transgenic technology is included in the invention, although mammals are preferred which include non-human primates, sheep, goats, horses, cattle, pigs, rabbits, and rodents such as mice, guinea pigs, hamsters, rats and gerbils.

Invention polypeptides can be used to generate additional reagents, such as antibodies. Thus, in accordance with the present invention, antibodies that bind to CFTR polypeptides having substitutions as set forth herein, fragments thereof and polypeptides having an AFT sequence are provided. Antibody comprising polyclonal antibodies, pooled monoclonal antibodies with different epitopic specificities, and distinct monoclonal antibody preparations, are provided. The invention antibodies can be used in diagnostic methods, purification methods and in the treatment methods, as disclosed herein.

The term "antibody" includes intact molecules as well as fragments thereof, such as Fab, F(ab')2, and Fv which are capable of binding to an epitopic determinant present in an invention polypeptide. Other antibody fragments are included so long as the fragment retains the ability to selectively bind with its antigen.

As used herein, the term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Generally, epitopes have at least five contiguous amino acids.

Antibodies that bind to invention polypeptides can be prepared using intact polypeptide or small peptide fragments thereof as the immunizing antigen. The polypeptide used to immunize an animal is derived from translated DNA or chemically synthesized, if desired, can be conjugated to a carrier protein. Such commonly used carriers that are chemically coupled to the immunizing peptide include, for example, keyhole limpet hemocyanin (KLH), thyroglobulin, bovine serum albumin (BSA), and tetanus toxoid.

Monoclonal antibodies are made by methods well known to those skilled in the art (Kohler et al., *Nature* 256:495, 1975; and Harlow et al., *Antibodies: A Laboratory Manual*, page 726, Cold Spring Harbor Pub., 1988). Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques which include, for example, affinity chromatography with Protein-A Sepharose, size-exclusion chromatography, and ion-exchange chromatography (see e.g., Coligan et al., "Production of Polyclonal Antisera in Rabbits, Rats, Mice and Hamsters," in: *Current Protocols in Immunology* sections 2.7.1-2.7.12 and sections 2.9.1-2.9.3; and Barnes et al., "Purification of Immunoglobulin G (IgG)," in: *Methods in Molecular Biology*, Vol. 10, pages 79-104, Humana Press, 1992).

The preparation of polyclonal antibodies is well-known to those skilled in the art (see, e.g., Green et al., "Production of Polyclonal Antisera," in: *Immunochemical Protocols*, pages 1-5, Manson, ed., Humana Press, 1992; Harlow et al., 1988, supra; and Coligan et al., 1992, supra, section 2.4.1).

Antibody fragments (e.g., Fab, F(ab')2, and Fv) of the present invention can be prepared by proteolytic hydrolysis of the antibody, for example, by pepsin or papain digestion of whole antibodies.

In accordance with the present invention, there are provided methods for identifying a therapeutic agent for treating cystic fibrosis. A method of the invention comprises contacting a cell expressing an export-incompetent CFTR with a test agent under conditions allowing an interaction between the agent and a factor mediating or contributing to export-incompetence, and determining whether the agent increases the amount of export-incompetent CFTR on the cell surface, where an increased amount of CFTR on the cell surface identifies a therapeutic agent for treating cystic fibrosis. Particular export-incompetent CFTRs that may be used include ΔF508 and R1066C.

In another embodiment, the invention provides methods for identifying an agent that induces or increases transport of an export-incompetent protein. A method of the invention comprises contacting an export-incompetent protein with a test agent under conditions allowing an interaction between the agent and a factor mediating or contributing to export-incompetence, and determining whether the agent increases the amount or the rate of protein transported, where an increased amount of the protein transported identifies an agent that induces or increases transport of an export-incompetent protein. In one aspect, the method is performed using a cell expressing an export-incompetent protein. In another aspect, the method is performed in vitro. In certain additional aspects, the export-incompetent protein is a cell surface protein, a secreted protein, a lysosomal protein or an endosomal protein. Such in vitro assays are described, for example, in Zhang et al. (*Nat Struct. Biol.* 5:180-183 (1998))

As used herein, the terms "transport" or "intracellular transport" describes the movement or progression of a molecule along the ER-golgi pathway. Thus, an induction or increase in "transport" means that the protein is transported from the ER to the cis-golgi, or beyond, e.g., to the medial-golgi, to the trans-golgi, to the cell surface or, as appropriate, secreted or, to the endosome or lysosome. It is specifically intended that the term transport involve movement from any point within the pathway to any point within the pathway. Preferably, an agent that induces or increases transport will promote movement of the protein to its final destination. For example, an agent that induces or increases CFTR transport will promote movement from the ER to the cell surface. Thus, an "increased rate of transport" or an "increase in the rate of transport" means that the time needed for transport is decreased and an "increase in an amount transported" means that the amount of protein transported is greater.

In the methods of the invention for identifying a therapeutic agent for treating CFTR, or for identifying an agent that induces or increases transport of an export-incompetent protein, an increase in an amount of the protein on the cell surface or an increase in an amount of protein transported will be detected. Various detection methods can be employed. For example, to detect an increase in an amount of protein on the cell surface, immunostaining with a specific antibody (e.g., anti-CFTR, M3A7), or direct visualization (e.g., a CFTR-GFP fusion) as disclosed herein, can be employed. Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface. To detect an increase in an amount of protein transported, methods that detect an increased amount of protein on the cell surface can be employed. Additionally, as disclosed herein, protein transport can be detected by the acquisition or removal of particular oligosaccharide chains. For example, endoH resistant oligosaccharide chains are acquired in the golgi. Thus, detection of endoH resistant chains provides a means with which to detect transport of protein from the ER to golgi. Later stages of transport (e.g., trans-golgi) are associated with the removal or addition of particular oligosaccharides from proteins. Thus, other glycosidases, such as endoglycosidase F, neuraminindase and the like can be used to detect whether an increase in protein transport to later stage,s such as the trans-golgi, for example, occurs. Such enzymes are commercially available (e.g., Boehringer Manheim Biochemicals, Indianapolis, Ind.) or are otherwise known in the art.

Polypeptide sequence motifs that mediate or contribute to ER retention of export-incompetent CFTR are disclosed herein. When cells that express export-incompetent ΔF508 CFTR are treated with polypeptides having a sequence motif such as R-X-R, an increase in CFTR transport from the ER to the cell surface is observed (see for example, FIG. 4).

Thus, in accordance with the present invention, there are provided methods for treating cystic fibrosis. A method of the invention comprises administering to a subject a pharmaceutical formulation comprising a polypeptide having an arginine framed peptide sequence in an amount effective for treating cystic fibrosis. In one aspect, the subject expresses an export-incompetent CFTR, such as ΔF508 or R1066C CFTR. In another embodiment, a method of the invention comprises administering to a subject a pharmaceutical formulation containing a CFTR, wherein at least one arginine of the arginine framed peptide sequence is substituted with an amino acid, in an amount effective for treating cystic fibrosis. The substituted CFTR can be wild-type CFTR, mutated CFTR, can be further modified, and can be encoded by a nucleic acid sequence, as disclosed herein. For example, a nucleic acid encoding a CFTR polypeptide having one or more amino acid substitutions of an R-X-R sequence can be administered to a subject afflicted with CF in order to treat CF. Other CFTR mutant sequences are known including, for example, ΔI507, N1303K, S549I, S549R, A559T, H139R, G149R, D192G, R258G, S949L, H949Y, H1054D, G1061R, L1065P, R1066C, R1066H, R1066L, Q1071P, L1077P, H1085R, W1098R, M1101K, M1101R, and can similarly be modified or substituted as set forth herein.

The fact that other proteins destined for the intracellular transport pathway frequently exhibit export incompetency due to mutations, or other factors, indicates that the transport of such export-incompetent polypeptides can be induced or increased by treating with a polypeptide having an AFT sequence. Accordingly, physiological disorders associated with export-incompetent proteins can similarly be treated.

Thus, in accordance with the present invention, there are provided methods for treating a subject having a physiological disorder associated with an export incompetent protein. A method of the invention comprises administering to the subject a pharmaceutical formulation comprising a polypeptide having an R-X-R sequence in an amount effective for treating a physiological disorder associated with an export-incompetent protein. In one aspect, the polypeptide has at least four amino acids or, in another aspect, at least seven amino acids. In certain other aspects of the invention method, the export incompetent protein is a cell surface protein, a secreted protein, a lysosomal protein or an endosomal protein.

Physiological disorders associated with an export incompetent protein that can be treated in a method of the invention include, for example, Stargardt's disease and particular types of macular dystrophy caused by mutations of the retinal rod transporter, ABC-R, resulting in deficiency of ER export. Additional candidate physiological disorders associated with various other ABC (adenine-nucleotide binding cassette) proteins.

The methods for treating a subject having a physiological disorder associated with an export incompetent protein can be practiced with the invention polypeptides having an AFT sequence based on the CFTR sequence, such as GYRQRLE (SEQ ID NO:1), EYRYRSV (SEQ ID NO:2), GQRARIS (SEQ ID NO:3) and QARRRQS (SEQ ID NO:4). Alternatively, the methods can be practiced using polypeptides having AFT sequence, including flanking sequences, if desired, based upon the amino acid sequence of the export incompetent polypeptide that causes or is associated with the physiological disorder being treated. In this way, increased specificity can be provided by using polypeptides having an AFT polypeptides sequence based on the polypeptide sequence. Increased specificity may decrease potentially deleterious side effects caused by inducing or increasing ER export of unrelated polypeptides, for example, by inhibiting the interaction of an ER retention factor with the unrelated protein thereby increasing its export.

As the invention polypeptides and nucleic acids are useful for treating physiological disorders associated with an export-incompetent protein, including cystic fibrosis, the present invention also provides pharmaceutical formulations comprising invention polypeptides and nucleic acids.

The compositions administered to a subject will be in a "pharmaceutically acceptable" or "physiologically acceptable" formulation. As used herein, the terms "pharmaceutically acceptable" and "physiologically acceptable" refer to carriers, diluents, excipients and the like that can be administered to a subject, preferably without excessive adverse side effects (e.g., nausea, headaches, etc.). Such preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobial, anti-oxidants, chelating agents, and inert gases and the like. Various pharmaceutical formulations appropriate for administration to a subject known in the art are applicable in the methods of the invention (e.g., Remington's Pharmaceutical Sciences, 18th ed., Mack Publishing Co., Easton, Pa., 1990 and The Merck Index, 12th ed., Merck Publishing Group, Whitehouse, N.J., 1996).

Controlling the duration of action or controlled delivery of an administered composition can be achieved by incorporating the composition into particles or a polymeric substance such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. The rate of release of the composition may be controlled by altering the concentration or composition of such macromolecules. For example, it is possible to entrap an AFT sequence in micro-capsules prepared by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The compositions administered by a method of the invention can be administered parenterally by injection or by gradual perfusion over time. The composition can be administered via inhalation, intravenously, intraperitoneally, intramuscularly, subcutaneously, intracavity, or transdermally, and preferably is administered intravascularly. The compositions can be administered in a single dose, or multiple doses. The doses needed for treating a physiological disorder associated with an export-incompetent protein will be sufficient to ameliorate some or all of the symptoms of the disorder. Such dosages can readily be determined by those skilled in the art (see for example, Ansel et al. *Pharmaceutical Drug Delivery Systems,* 5th ed. (Lea and Febiger (1990), Gennaro ed.).

The AFT polypeptides increase export incompetent CFTR cell surface expression. Although not wishing to be bound by any particular theory, it is reasonable to assume that the mechanism by which the AFT polypeptide sequence increases export is by competitively inhibiting binding of an ER retention factor to its recognition site. As used herein, the term "ER retention factor" refers to any biological molecule, such as a protein, macromolecule, macromolecular machinery or organelle that mediates or contributes to a protein's retention in the ER, as assessed by an inability or delay in active or passive export or egress of the protein from the ER.

It is possible that such an ER retention factor may also recognize signals other than an AFT. Thus, even though an export-incompetent protein lacks an AFT sequence, polypeptides having an AFT sequence may still competitively inhibit an ER retention factor thereby inducing or increasing transport of a protein that does not have an AFT sequence.

Thus, in another embodiment, the invention provides methods for inducing or increasing intracellular transport of an export-incompetent protein in a cell. A method of the invention comprises contacting a cell with a composition comprising a polypeptide having an R-X-R sequence in an amount sufficient for inducing or enhancing intracellular transport of the export-incompetent protein. In one aspect, the export-incompetent protein has an AFT sequence. In certain other aspects, the export incompetent protein is secreted or is a cell surface protein.

Any cell can be employed in a method of the invention for identifying a CF therapeutic agent or for identifying an agent that induces or increases transport of an export-incompetent protein, so long as the cell expresses or is made to express an export-incompetent protein.

In another embodiment, there are provided methods for identifying an agent that inhibits or disrupts an interaction between an R-X-R polypeptide and an ER retention factor. A method of the invention comprises incubating an R-X-R polypeptide and an ER retention factor under conditions allowing their interaction; adding a test agent to the incubation; and detecting binding between said R-X-R polypeptide and said ER retention factor, where decreased binding in the presence of the test agent identifies an agent that inhibits or disrupts an interaction between an R-X-R polypeptide and an ER retention factor.

As used herein, the term "incubating" refers to conditions that allow the contact, binding or interaction between a polypeptide, functional fragment or polynucleotides encoding same and the test agent. The term "contacting" as used herein includes in solution, in solid phase, in cells and in an animal.

A therapeutic agent for treating CFTR or other physiological disorders associated with an export-incompetent protein, as well as agents that induce or increase transport of an export-incompetent protein and agents that inhibit, prevent or disrupt the interaction between an R-X-R polypeptide and an ER retention factor can essentially be any molecule. Generally the agent will be a small organic molecule (e.g., a peptide) capable of interacting with either an appropriate polypeptide or ER retention factor such that the agent competitively or non-competitively inhibits, interferes with or antagonizes, partially or completely, the interaction. An example of a competitive antagonist would be an agent that binds to an ER retention factor at the site of interaction with the polypeptide that subsequently prevents interaction with the polypeptide. Alternatively, a competitive antagonist can bind to an ER retention signal present on a polypeptide, such as an AFT, with which the ER retention factor interacts, thereby preventing or inhibiting its interaction with an ER retention factor. An example of non-competitive antagonist would be an agent that binds either an ER retention factor or a polypeptide containing an appropriate retention signal, but does not prevent or inhibit its interaction. Nevertheless, such a non-competitive antagonist prevents or inhibits ER retention of the complex, thereby promoting export.

Although such agents will generally directly interact with the ER retention factor or the polypeptide with which the ER retention factor interacts, agents that function indirectly also are contemplated. For example, an indirect agent may activate or increase an interaction between a polypeptide and a factor that contributes to or mediates ER export, thereby inducing or increasing transport from the ER Further included are agents that function through any enzymatic interaction in which the agent directly or indirectly performs a biochemical modification (e.g., phosphorylation) of the polypeptide or ER retention factor that results in inhibiting or blocking ER retention. For example, post-translational modification of an amino acid sequence near an AFT sequence may prevent or inhibit its interaction with an ER retention factor. Thus, agents that directly or indirectly alter polypeptides, such as to increase or decrease phosphorylation, ubquitination, glycosylation, proteolytic cleavage and the like are therefore included.

AFT polypeptides also can be employed to identify an ER retention factor. Thus, the invention further provides a method for identifying an ER retention factor. A method of the invention comprises contacting a composition suspected of containing an ER retention factor with a polypeptide having an R-X-R sequence under conditions allowing their interaction and detecting binding between the factor and the polypeptide, thereby identifying an ER retention factor. The method can be performed in vitro. The method also can employ polypeptides having various lengths as set forth herein. Specific polypeptides include GYRQRLE (SEQ ID NO:1), EYRYRSV (SEQ ID NO:2), GQRARIS (SEQ ID NO:3) and QARRRQS (SEQ ID NO:4).

In various other embodiments, the invention also provides methods for inhibiting degradation of a protein in a cell. A method of the invention comprises contacting a cell with a polypeptide having an R-X-R sequence in an amount sufficient for inhibiting degradation of a cell surface or secreted protein. The invention also provides methods for detecting the presence of an export-incompetent protein in a cell. A method of the invention comprises contacting a cell with a polypeptide having an R-X-R sequence and detecting the intracellular transport of the protein. The various assays for detecting transport have been set forth herein, using an enzymes, such as endoglycosidases, cell surface immunolabeling etc. Such methods are equally applicable in a method for detecting the presence of an export-incompetent protein in a cell.

In accordance with the present invention, there are provided kits for treating subjects having or suspected of having a physiological disorder or condition associated with an export-incompetent protein. A kit of the invention contains one or more AFTs or a polypeptide containing an AFT sequence, and a label or packaging insert for treating a physiological disorder associated with an export-incompetent protein as set forth herein in suitable packaging material. In various aspects, the kits contain R-X-R tripeptides, preferably polypeptides having an R-X-R sequence at least 4 amino acids long, more preferably polypeptides having an R-X-R sequence at least 5 amino acids long, and most preferably polypeptides having R-X-R sequence at least 6 amino acids or longer. It is understood that any invention polypeptide can be included in the kits of the invention. Particular embodiments include peptides having the sequences GYRQRLE (SEQ ID NO:1), EYRYRSV (SEQ ID NO:2), GQRARIS (SEQ ID NO:3) and QARRRQS (SEQ ID NO:4).

As used herein, the term "packaging material" refers to a physical structure housing the components of the kit, such as invention polypeptides and nucleic acids. The packaging material preferably maintains the components sterilely, and can be made of material commonly used for such purposes (e.g., paper, corrugated fiber, glass, plastic, foil etc.). The label or packaging insert indicates that the kit is to be used in a method of the invention, for example, for treating CF.

As disclosed herein, the substitution of wild-type CFTR arginine framed peptide sequence or other signaling motifs in the C-terminal extension domain may increase transport of the substituted wild-type CFTR over unsubstituted wild-type CFTR. Thus, an amount of CFTR transported to the cell surface can be increased by such substitutions, even in an export-competent wild-type CFTR. Accordingly, it is contemplated that substituted polypeptides that utilize the intracellular transport pathway can be produced in greater amounts than unsubstituted polypeptides by virtue of this increased transport. For example, secretion of a recombinant polypeptide can be increased by substituting an arginine framed peptide or one of the C-terminal extension motifs in the protein.

Thus, in accordance with the present invention, there are provided methods for increasing the biological production of recombinant polypeptides. A method of the invention comprises transforming a host with a nucleic acid encoding a recombinant polypeptide having a substituted arginine framed peptide sequence under conditions allowing production in an amount greater than unsubstituted polypeptide, thereby increasing biological production of the recombinant polypeptide.

As used herein, the term "biological production" refers to the production of a polypeptide by a living cell, tissue, organ or entire organism, such as an animal. The methods of the invention for increasing the biological production of useful polypeptides can be applied to naturally occurring cell surface, secreted, endosomal or lysosomal polypeptides. Additionally, the production of polypeptides engineered to utilize the intracellular transport pathway, by attaching an intracellular transport targeting sequence, for example, can similarly be increased.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims. The invention is further described in the following examples, which do not limit the scope of the invention(s) described in the claims.

EXAMPLE I

This example shows that particular signaling motifs mediate or contribute to the export incompetent characteristic of ΔF508 CFTR.

Inspection of the CFTR amino acid sequence reveals four arginine-framed tripeptide (AFT) sequences, one in the N-terminal cytoplasmic domain, two in the first nucleotide-binding domain (NBD1) and one in the R-domain (FIG. 1A). Because of the sensitivity of CFTR to misprocessing due to missense mutations in its cytoplasmic domains (Seibert, F. S et al. (1995) *J. Biol. Chem.* 270:2158-2162) the most conservative substitutions of these triplets i.e. substitutions of a lysine for the arginine at position 1 or 3, were made (FIG. 1B).

Each of the arginine to lysine substitutions were introduced into plasmids containing either the wild-type or ΔF508 CFTR sequences. Briefly, a full-length human CFTR cDNA in pNUT vector (Chang, X.-B. et al. (1993). *J. Biol. Chem.* 268:11304-11311) was utilized as a template for site-directed mutagenesis (QuickChange Site Directed Mutagenesis Kit, Stratagene, La Jolla, Calif.) by polymerase chain reaction (PCR) according to the manufacturer's recommendation. The following oligonucleotides were used to introduce R29K, R516K, R555K and R766K into wild-type CFTR cDNA. R29K: CAATTTTGAGGAAAGGATACA AACAGCGCCTGGAATTGTCAG (SEQ ID NO:10) and CTGACAATTCCAGGCGCTGT TTGTATCCTTTCCTCAAAATTG (SEQ ID NO:11); R516K: CCTATGATGAATATAAATACAGAAGCCTCATC (SEQ ID NO:12) and GATGACGCTTCTGTAT TTATATTCATCATAGG (SEQ ID NO:13); R555K: GGAG-GTCAACGAGCAAAAATTTCTTTAGCAAGAG (SEQ ID NO:14) and CTCTTGCTAAAGAAATT TTTGCTCGTTGACCTCC (SEQ ID NO:15); R766K: CTTCAGGCACGAAGGAAGCAGTCTCTCCTGAACC (SEQ ID NO:16) and GGTTCAGGACAGACTGC TTCCTTCGTGCTGAAG (SEQ ID NO:17). To combine four lysine substitutions in one cDNA, the following fragments were prepared: Dra III-Kpn I fragment which contains part of wild-type CFTR cDNA from nt 3328 to 4721 and most of the pNUT expression vector; Kpn I-Afl II fragment which contains part of the pNUT expression vector and part of CFTR from nt 72 to 993 covering the R29K mutation; Afl II-Dra III fragment from nt 994 to 1777 covering the R516K substitution; Dra III-EcoR I fragment from nt 1778 to 2230 covering the R555K substitution; and EcoR I-Dra III fragment from nt 2231 to 3327 covering the R766K substitution. These five fragments were ligated together to generate full length CFTR cDNA in pNUT (T4 DNA ligase, New England Biolabs, Beverly, Mass.). The sequences of the four fragments covering these substitutions were verified after insertion into the pNUT-CFTR. To combine the cystic fibrosis causing mutation, ΔF508, with each individual or all four of the above substitutions, the same strategy was utilized, except that pNUT-ΔF508 CFTR was utilized as template. pNUT-ΔF508 CFTR/R29K was made by ligating the following three fragments together, Kpn I-Afl II fragment which contains part of pNUT vector and part of CFTR from nt 72 to 993 covering the R29K substitution, Afl II-Hpa I fragment from nt 994 to 2463 covering the ΔF508 substitution, and Hpa I-Kpn I fragment which contains the part of CFTR from nt 2464 to 4721 and part of the pNUT vector. The sequences covering ΔF508, R29K, R516K, R555K and R766K were verified after insertion into the expression vector pNUT.

Baby hamster kidney cells (BHK) cells grown at 37° C. in 5% $CO_2$ were employed as hosts for CFTR expression as described previously (Loo et al. (1998) *EMBO J.* 17:6879-6887; and Seibert, F. S et al. (1995) *J. Biol. Chem.* 270:2158-2162). Subconfluent BHK cells were transformed with the above wild-type or ΔF508 CFTR constructs using calcium phosphate precipitation (Chen, C., and Okayama, H. (1987) *Mol. Cell. Biol.* 7: 2745-2752). After growth in selective media containing 500 μM methotrexate, individual colonies were picked and amplified in the same selective media.

BHK cells were grown, collected and then lysed with 1% SDS; the DNA was sheared by cycling through a 22 gauge needle. Protein lysate (20 μg) from the sample were then subjected to SDS-PAGE on 7% polyacrylamide gels. Protein was electroblotted from the gel to nitrocellulose membrane and the membrane was probed with a mouse anti-CFTR monoclonal antibody, M3A7 (Kartner, N. et al. (1992) *Nat. Genetics* 1:321-7). Chemiluminescent detection was performed according to the manufacturer's recommendations (Pierce).

For endoglycosidase H treatment, cell lysates were diluted with 10 volumes of buffer (50 mM sodium acetate, pH 5.3, 0.5% Nonidet P-40, 1% β-mercaptoethanol plus a protease inhibitor mixture: 2 μg/ml aprotinin, 120 μg/ml benzamidine, 3.5 μl E64, 1 μg/ml leupepetin and 50 μg/ml pefabloc). This yielded a final SDS concentration of 0.1%. Samples were then incubated for 4 hr at 37° C. with 10 mU of endoglycosidase H (Boehringer Mannheim). The reactions were stopped by addition of 4 volumes of cold ethanol (−20° C.) to precipitate the proteins. Precipitated proteins were then resuspended in gel loading dye and subjected to SDS-PAGE and immunoblotting as above.

Figure 2A:
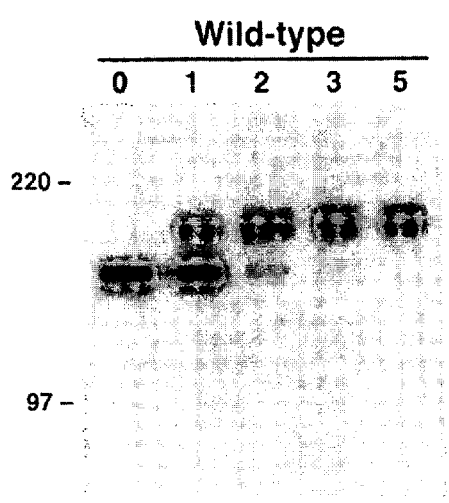
FIGS. 2A to 2D show the maturation of A) wild-type CFTR; B) wild-type CFTR with arginine to lysine substitutions at all four arginine-framed tripeptides (wild-type/4RK; C) ΔF508 CFTR and; D) ΔF508 CFTR with arginine to lysine substitutions at all four arginine-framed tripeptides (ΔF508/4RK). Cells were pulse-labeled for 20 min and the chase times in hours are indicated. Maturation was assessed by the acquisition of endoglycosidase H resistant oligosaccharide chains, which results in a decrease in the corresponding proteins mobility on SDS-PAGE.
Figure 2B:
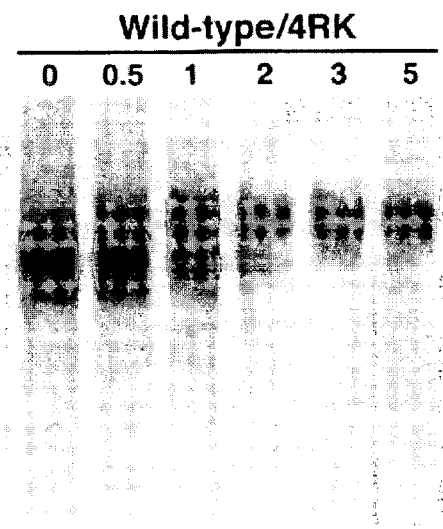

Western blots of BHK cell extracts revealed that these four R→K substitutions individually or in combination did not dramatically change the steady state amounts of mature, fully glycosylated band (~170 kDa) or immature core-glycosylated band (~150 kDa) of wild-type CFTR (FIG. 1C, lanes 1-6). Thus, synthesis and processing was not impaired by any of these mutations. In the case of ΔF508 CFTR, however striking changes were observed. Without any additional mutation, it displays the usual doublet band pattern with the same major core-glycosylated band (~150 kDa) as the wild-type plus a smaller band at ~135 kDa (lane 7). The latter is missing an N-terminal fragment of ~15 kDa due to alternative initiation of translation or a specific proteolytic clip and is much more prominent in mutants such as ΔF508 than in wild-type CFTR This band remains prominent in 3 of the 4 R→K variants (R516K, R555K, R766K; lanes 9, 10, and 11 respectively) but not in R29K (lane 8) or in "4RK (lane 12)."

More significantly, however, bands of lower mobility are produced by the R29K and 4RK variants (lanes 8 and 12). These are not identical in size but they appear to be at either edge of the broad band displayed by wild-type CFTR because of heterogeneous N-glycosylation. The relative amount is greater in the 4RK combination mutant.

Figure 1D:
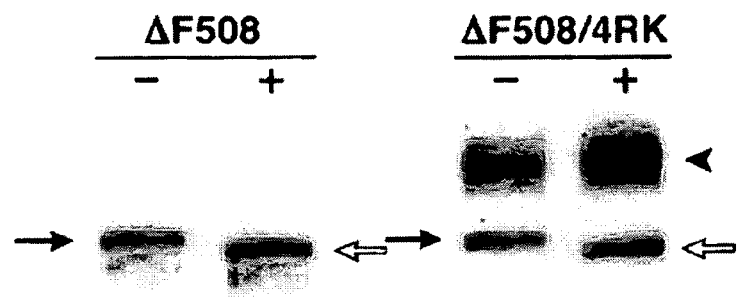

Endoglycosidase-H insensitivity of these large bands formed by the R29K and 4RK versions of ΔF508 CFTR confirms that indeed their oligosaccharide chains have been extended by Golgi glycosyl transferases (FIG. 1D, arrowhead). Further evidence that these bands were present at the cell surface came from their accessibility to an impermeant amino reactive biotinylation reagent added to intact cell monolayers. Therefore, substitution of one of the obligatory arginines, in the RQR triplet is able to partially overcome the maturation arrest of ΔF508; this effect is much more pronounced when similar substitutions are made in all four triplets.

For cell surface biotinylation studies, cells grown to about 90% confluency were treated with 2 mM sodium butyrate for 18 h to augment CFTR expression. Dishes of cells were then placed on ice in a cold room for 30 minutes and all subsequent steps were performed. Cells washed with PBS containing 0.1 mM $CaCl_2$ and 1.0 mM $MgCl_2$, were labeled using 3 ml of 1 mg/ml EZ-Link Sulfo-NHS-SS-biotin (Pierce) in PBS, pH 8.0 for 30 minutes. Following washes in PBS+1% BSA and PBS, cells were incubated for 30 minutes in NP40 lysis buffer (0.09% NP40, 150 mM NaCl, 10 mM $NH_4MoO_4$, 50 mM Tris-HCl, pH 7.4), scraped and transferred to microfuge tubes. Insoluble materials were removed by centrifugation. Biotinylated proteins were then precipitated by incubation overnight with 50 μl of packed immobilized streptavidin beads (Pierce). Beads were washed with RIPA buffer (0.1% SDS, 1% DOC, 1% Triton X-100, 150 mM NaCl, 50 mM Tris-Hcl, pH 7.4) and proteins eluted with gel sample buffer for electrophoresis and Western blotting with M3A7 as detailed above.

The results in FIG. 1D show that the mature band of substituted ΔF508 CFTR (ΔF508/4RK) was accessible to the impermeant amino reactive biotinylation reagent added to the intact cell monolayers. These results confirm that substitution of AFTs can overcome the biosynthetic arrest of ΔF508 CFTR

EXAMPLE II

This example shows that export of substituted wild-type and ΔF508 CFTR from the endoplasmic reticulum and subsequent maturation is kinetically increased in comparison to unsubstituted wild-type and ΔF508 CFTR.

Pulse chase studies were performed to determine the rate at which maturation occurred in the arginine-framed triplet substituted wild-type and ΔF508 CFTR polypeptides (FIG. 2). Briefly, cells expressing unsubstituted and substituted wild type or ΔF508 CFTR were starved for 30 minutes by incubation in methionine-free medium and then labeled for 20 minutes with 100 μCi/ml of $^{35}$S-methionine (>800 Ci/mmol; Amersham). Cells were lysed at the end of the labeling period (0 chase time) or were further incubated in complete medium containing 5% fetal bovine serum and 1 mM methionine for the indicated times (chase). Cells were collected and lysed with the NP40 lysis buffer described above and centrifuged at 15,000×g for 15 min at 4° C. to obtain a soluble supernatant which was incubated overnight with the M3A7 primary antibody. Protein G-agarose (Gibco-BRL) was then used to remove the complexes formed which were washed four times with RIPA buffer, dissolved in electrophoresis sample buffer, and subsequently fractionated on SDS-7% acrylamide gels. Following fractionation, the gels were fixed in 30% methanol and 10% acetic acid, equilibrated in 1M sodium salicylate and dried for fluorography. Electronic autoradiography was performed with a Packard Instant Imager. Conversion of $^{35}$S-methionine pulse labeled precursor form of CFTR (time 0) to mature product after chase times (1, 2, 3 and 5 hour) are indicated.

At the end of the 30 min pulse (0 min), maturation of the wild-type CFTR precursor substituted with four lysine substitutions (wild-type/4RK) was already evident. In contrast, no maturation for unsubstituted wild-type CFTR was observed at the end of the pulse (compare FIG. 2A to 2B).

Figure 2C:
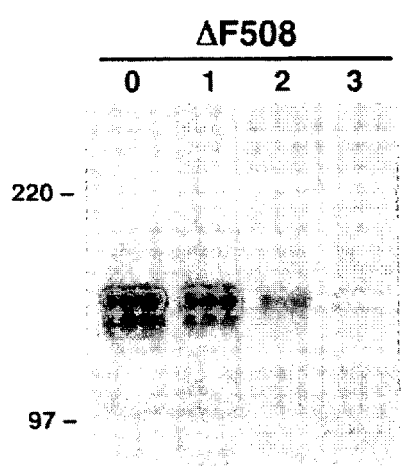
Figure 2D:
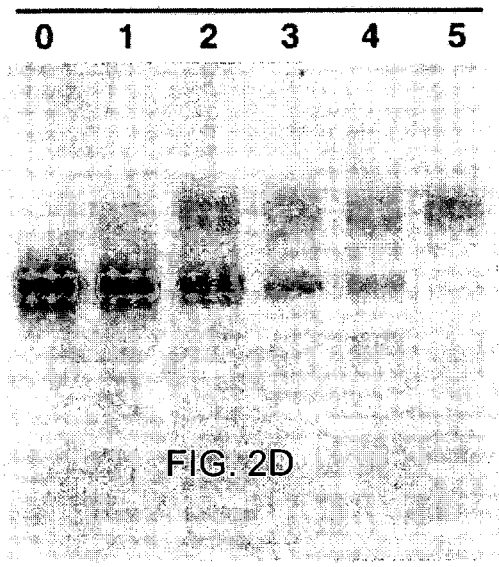

Conversion of the substituted ΔF508/4RK CFTR precursor to mature endoH resistant oligosaccharide chains is readily apparent whereas with ΔF508 CFTR, there is no conversion of the core-glycosylated precursor to any higher molecular weight product (compare FIG. 2C to 2D). Electronic autoradiography of the same dried gels indicated that approximately 10% of the radioactivity in the pulse-labeled immature ΔF508/4RK band (0 time) was present in the larger mature band after 4 h of chase (FIG. 2D). This compares with ~30% conversion of precursor to product in the case of wild-type CFTR. Hence, the extent of maturation of ΔF508/4RK viewed in this way is generally similar to the steady-state proportion reflected in the immunoblots (FIG. 1C). Furthermore, substitution of all four AFTs markedly decreased degradation and promoted maturation of ΔF508.

These results indicate that the rate of ER export of export-competent and export-incompetent polypeptides such as CFTR can be increased by substitution of AFT sequences as set forth herein.

EXAMPLE III

This example shows that increased maturation of substituted wild-type and ΔF508 CFTR can be observed directly in cells.

Immunofluorescence microscopy in cells expressing ΔF508 CFTR was performed using the highly specific monoclonal antibody, M3A7 (Kartner et al., 1992, supra). Briefly, transformed cells were grown on coverslips, fixed in 70% cold methanol at −20° C. for 10 minutes, blocked using 1% BSA and 5% normal rabbit serum in PBS and were permeabilized by incubating in PBS+0.1% saponin for 1 h at 4° C. CFTR was detected by incubation with 10 µg/ml of M3A7 primary antibody for 60 min at room temperature. Rhodamine linked rabbit anti-mouse secondary antibody (DAKO) was diluted 1:50 in the same blocking solution for a further 1 h incubation. Photomicrographs were made using a Diagnostic Instruments Spot Cam digital camera on a Nikon Microphot-FXA microscope.

Figure 3A:
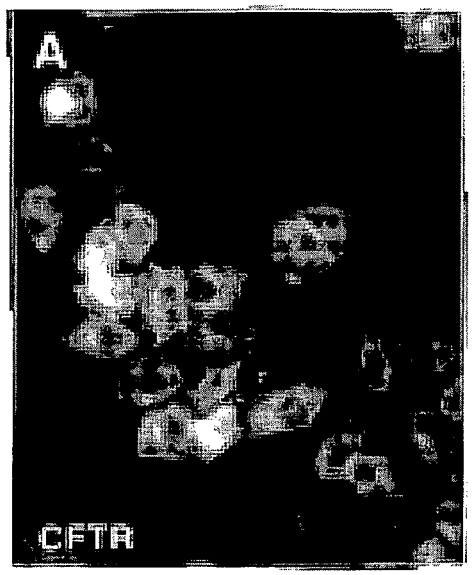
FIGS. 3A to 3D show the localization of A) wild-type CFTR; B) wild-type CFTR with arginine to lysine substitutions at all four arginine-framed tripeptides; C) ΔF508 CFTR and; D) ΔF508 CFTR with arginine to lysine substitutions at all four arginine-framed tripeptides, as determined by indirect immunofluorescence.
Figure 3B:
Figure 3C:
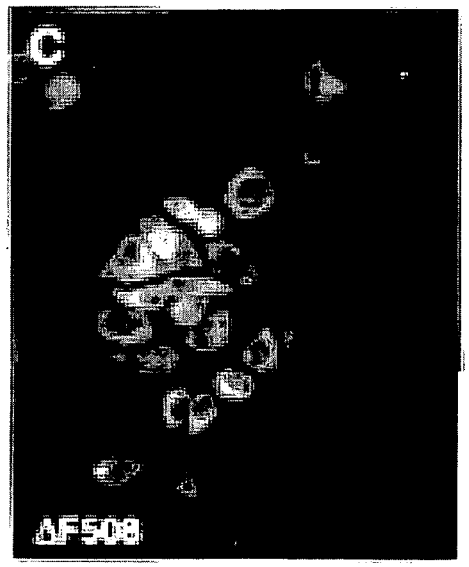
Figure 3D:
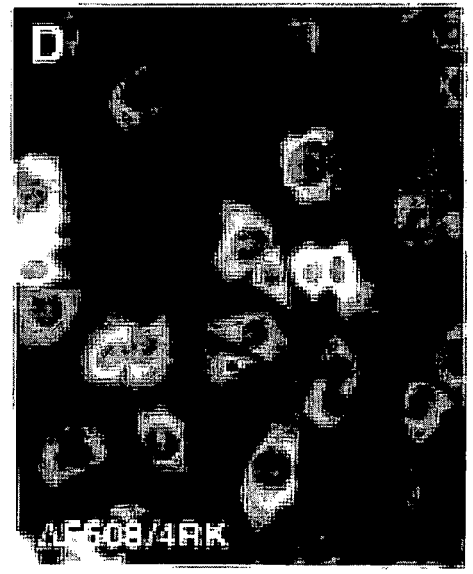
Figure 4A:
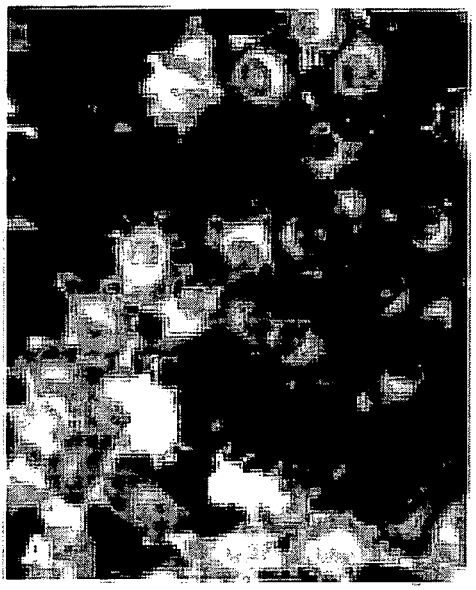
FIGS. 4A to 4D show the effect of AFT-containing heptamers on cells expressing wild-type CFTR-GFP fusion protein and ΔF508 CFTR-GFP fusion protein. A) cells expressing wild-type CFTR-GFP fusion protein, not exposed to AFT-containing heptamer peptides; B) cells expressing wild-type CFTR-GFP fusion protein, exposed to AFT-containing heptamer peptides; C) cells expressing ΔF508 CFTR-GFP fusion protein, not exposed to AFT-containing heptamer peptides; D) cells expressing ΔF508 CFTR-GFP fusion protein, exposed to AFT-containing heptamer peptides.
Figure 4B:
Figure 4C:
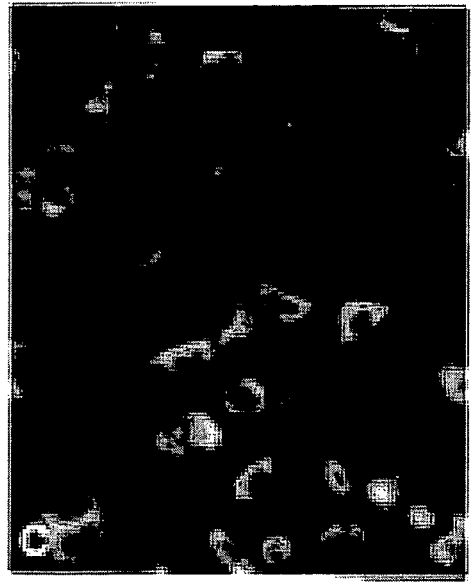
Figure 4D:
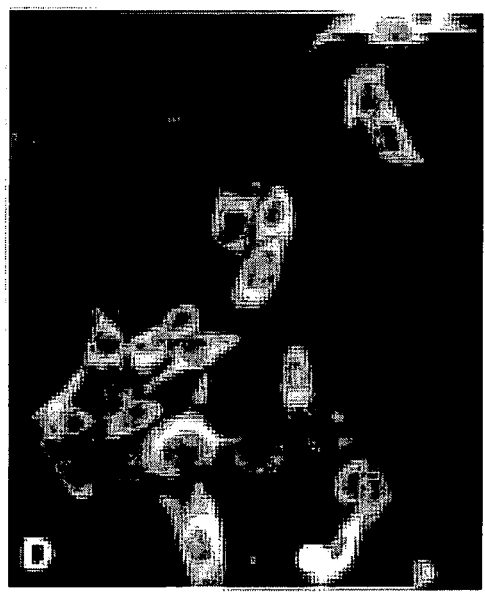

The results in FIG. 3 indicate that four R→K substitutions of wild-type CFTR does not alter its normal distribution, with perinuclear staining indicating ER localization of the immature CFTR in addition to strong uniform staining of mature CFTR over the entire cell surface (FIGS. 3A and 3B). Perinuclear staining only was observed in cells expressing ΔF508 CFTR indicating ER retention (FIG. 3C). In contrast, there is extension of the staining more peripherally in cells expressing ΔF508/4RK CFTR (FIG. 3D). Although there is still less peripheral staining for ΔF508/4RK CFTR than for wild-type CFTR, this is expected based upon the relative amounts of the mature CFTR with complex oligosaccharide chains (FIG. 1C and FIG. 2).

EXAMPLE IV

This example shows that polypeptides containing an AFT sequence can induce or enhance transport of export incompetent ΔF508 CFTR from the endoplasmic reticulum to the cell surface.

Heptamer peptides including two residues from the CFTR sequence on either side of the AFT were synthesized (Molecular Biology Core of the Mayo Clinic, Rochester, Minn.). BHK cells expressing either wild-type or ΔF508 CFTR-GFP fusion protein (Loo et al., 1998, supra) were allowed to take up a mixture of the heptamers by scrape loading (Malcolm et al., (1996) *J. Biol. Chem.* 271:13135-9) and plated on cover slips for visualization the next day using a fluorescence microscope with an FITC filter. Localization of wild-type CFTR-GFP fusion with or without exposure to heptamers was the same as antibody staining of wild-type CFTR. Cells expressing the ΔF508 CFTR-GFP fusion protein in the absence of heptamers also exhibited the same perinuclear clustering as was observed with antibody staining of unfused ΔF508 CFTR. In contrast, heptamer treatment of cells expressing the ΔF508 CFTR-GFP fusion protein exhibited more peripheral fluorescence staining.

The results in FIG. 4 show that an AFT sequence can competitively inhibit recognition of AFT containing nascent polypeptides thereby inhibiting ER retention and promoting transport of polypeptides containing AFT sequence from the endoplasmic reticulum.

EXAMPLE V

This example shows that the R→K substitutions result in a functionally active ΔF508 CFTR at the cell surface.

Wild-type and ΔF508 CFTR expressing cells with each of the individual R□K substitutions, or all four lysine substitutions were grown to confluence in six well culture dishes. The cells were washed with a modified Ringer's buffer solution (136 mM NaNO$_3$, 3 mM KNO$_3$, 2 mM Ca(NO$_3$)$_2$, 2 mM Mg(NO$_3$)$_2$, 10 mM glucose and 20 mM HEPES, pH 7.4) and loaded for 60 min at room temperature with the same buffer supplemented with 1 µCi Na$^{36}$Cl (Amersham) in a volume of 0.5 ml per well. Wells were then washed three times at one min intervals. Samples (0.5 ml) were then collected at 1 minute intervals for scintillation counting with stimulation occurring at time 0 by adding buffer containing 1 mM IBMX, 10 µM Forskolin and 100 µM dibutyryl cyclic AMP. The 0.5 ml samples were collected into 24 well Top Count plates (Packard) and 1 ml of Microcint 40 scintillation cocktail (Packard) was added. $^{36}$Cl⁻ radioactivity was determined in a Packard Top Count scintillation counter.

Figure 5A:
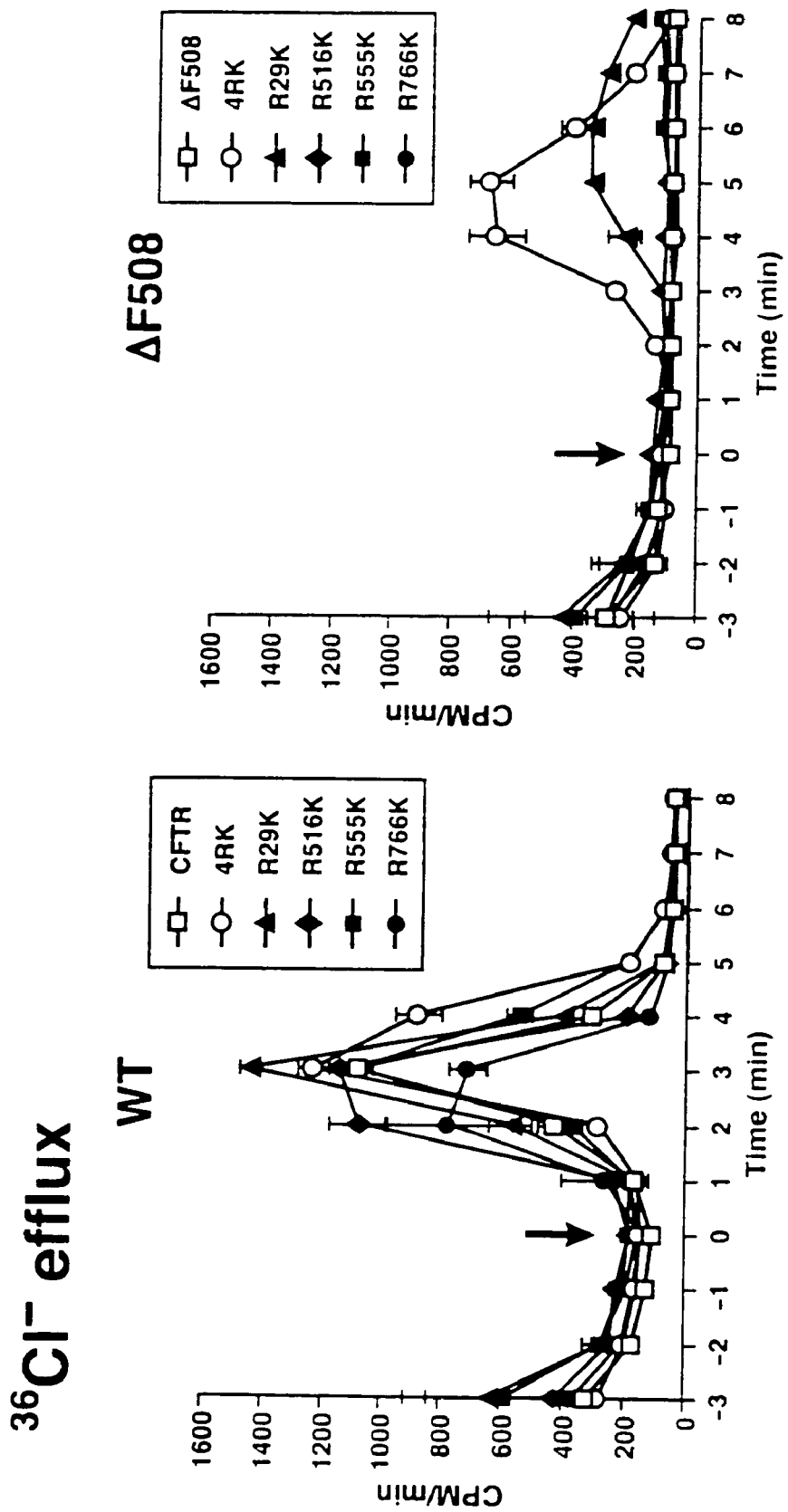
FIGS. 5A and 5B show the effect of the arginine to lysine substitutions on CFTR chloride channel activity from A) cells expressing wild-type and ΔF508 CFTR with or without AFT mutations ($^{36}Cl^-$ efflux in cpm/min) and B) single CFTR $Cl^-$ channels in planar lipid bilayers isolated from cells expressing wild-type, wild-type/4RK and ΔF508/4RK CFTR. The studies in A) were performed in triplicate, samples were averaged and the vertical bars represent standard deviation. In B), the arrows indicate stimulation with Forskolin and all points histograms are shown to the left of the tracings.

The influence of each of the R→K substitutions on the cAMP stimulated efflux of $^{36}$Cl⁻ from wild-type or ΔF508 CFTR expressing cells loaded with $^{36}$Cl⁻ anion is shown in FIG. 5A. Within 3 minutes of cAMP stimulation there was a maximal rate of efflux from all cells expressing wild-type CFTR with or without any or all of the R→K mutants. No detectable increase in efflux rate from cells expressing ΔF508 CFTR alone or with the R516K, R555K or R766K substitution was observed. In cells expressing ΔF508/R29K, low rates of $^{36}$Cl⁻ efflux occurred at delayed times after stimulation. In cells expressing ΔF508 CFTR combined with all four R→K substitutions (4RK) the maximal rates of efflux observed were more than half as rapid as those from cells expressing wild-type CFTR, confirming that mature ΔF508/ 4RK CFTR does function at the cell surface.

To further characterize the Cl⁻ channel activity, membrane vesicles were isolated from cells expressing wild-type, wild-type/4RK and ΔF508/4RK CFTR, fused with planar lipid bilayers and single channels were recorded (Aleksandrov, A. A., and Riordan, J. R. (1998) *FEBS Lett.* 431:97-101). Vesicles were prepared and phosphorylated with PKA as described previously (Aleksandrov and Riordan, 1998, supra). Briefly, planar lipid bilayers were painted onto a 0.2 mm hole drilled in a Teflon cup using a phospholipid solution in n-decane containing a 2:1 mixture of 1-palmitoyl-2-oleoyl-sn-glycero-3-phosphoethanolamine and 1-palmitoyl-2-oleoyl-sn-glycero-3-phosphoserine (20 mg/ml). The lipid bilayer separated 1.0 ml of solution in the Teflon cup (cis-side) from 4.0 ml of solution in an outer glass chamber (trans-side). Both chambers were magnetically stirred and thermostated. Heating and temperature control were established using a Temperature Control System TC2BIP (Cell Micro-Controls). Electrical contact with the solutions was provided by Ag/AgCl electrodes through agar bridges filled with 0.5 M KCl. The membrane potential difference was measured as the difference between trans and cis side potentials. The trans side was grounded and electrical measurements of the single channel current were performed under voltage clamp conditions using an Axopatch 200B (Axon Instruments) amplifier. The output signal was filtered with an 8-pole low pass Bessel Filter LPBF-48DG (NPI Electronic GmbH) with cut off frequency of 50 Hz and recorded on magnetic tape using a VR-10B (Instrutech Corp.) digital data recorded on a Sony SLV-440 VCR. For data analysis, the signal was digitized (Digidata 1200; Axon Instruments) with a sampling rate of 500 Hz and analyzed using pCLAMP 6.0 (Axon Instruments) software. Origin 4.0 (Microcal) software was used to fit all points histograms by multi-peak Gaussians. Membrane vesicles were prephosphorylated with PKA and added as a concentrated stock solution to the cis side to obtain a final protein concentration of 10-15 μg/ml. Measurements were made in symmetrical salts solutions containing, in mM: 300 Tris-HCl, 2 MgCl, 1 EGTA, pH=7.2, at a membrane potential of −75 mV. MgATP (2 mM) was added to the cis side only. Under these conditions any cationic channels present in the membrane vesicles are invisible and CFTR chloride channels appeared only after fusion of vesicles with an inside out orientation. Conductances for wild-type, wild-type/4RK and ΔF508/4RK were 10.7, 10.8, and 10.7 pS, respectively. Mean open times $\tau_o$ were 230, 1400, and 700 msec respectively. Short mean closed times $\tau_{c1}$ were 10 msec in each case. Long mean closed times $\tau_{c2}$ were 680, 2000, and 2800 msec, respectively. Conductance as a function of Cl⁻ concentration and temperature as well as anion selectivity of the CFTR ion channel were tested in control experiments showing good agreement with published data (Tabcharani, J. A et al. (1997) *J. Gen. Physiol.* 110:341-54).

Figure 5B:
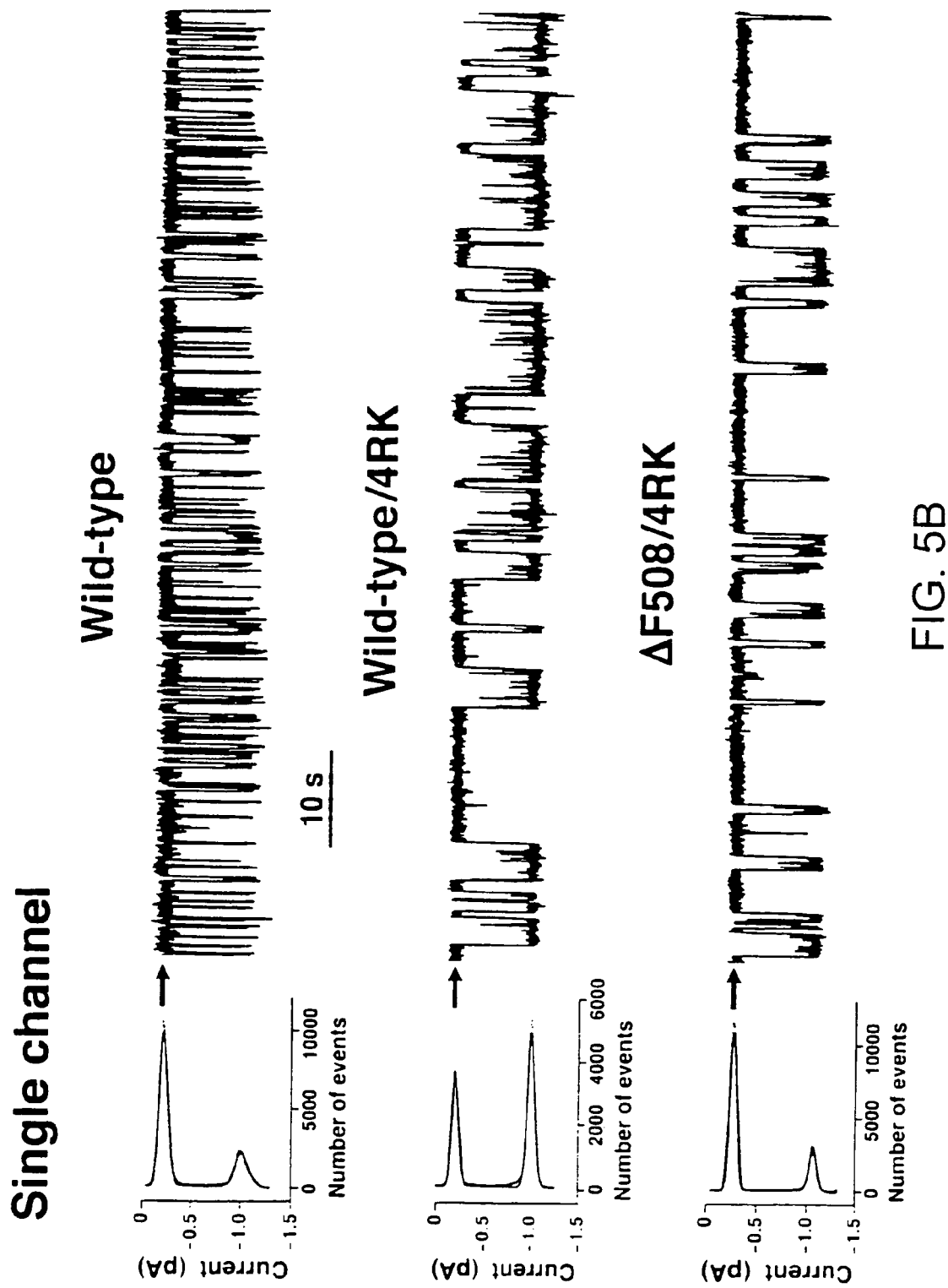

Compared with wild-type single channels which exhibit an open probability of ~0.25 at 25° C., channels generated by wild-type/4RK had a higher mean open probability of ~0.61 (FIG. 5B). Thus although the gating kinetics are somewhat altered with both mean open and mean closed times increased, the four R→K substitutions certainly do not impede current flow through the channel, consistent with the undiminished rate of ion flux (FIG. 5A). Significantly, the ΔF508/4RK channels had an open probability similar to wild-type CFTR, confirming the activity revealed by the macroscopic flux measurements. No tracing is shown for ΔF508 CFTR alone as we have never been able to detect CFTR-like single channels using vesicles from BHK cells expressing this variant. We conclude that the channels observed from ΔF508/ 4RK CFTR are entirely due to the maturation that is enabled by the release from ER retention when the AFTs are substituted.

The above examples show that substitution of one of the arginines in each of the four AFTs, individually or simultaneously, permits nascent ΔF508 CFTR to mature about one-third as efficiently as wild-type CFTR and generates functional chloride channels at the cell surface. Thus, release of ΔF508 CFTR from ER retention by interfering with recognition of these tripeptide signals may provide the basis of a novel therapeutic strategy for cystic fibrosis.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inhibiting degradation of a protein in a cell comprising contacting a cell with a Cystic Fibrosis Transmembrane Conductance Regulator (CFTR) polypeptide fragment having an R-X-R sequence in an amount sufficient for inhibiting degradation of a CFTR protein.

2. A method for detecting the presence of an export-incompetent protein in a cell comprising contacting a cell with a polypeptide comprising SEQ ID NO:1-4 and detecting the intracellular transport of the protein, wherein the protein is a Cystic Fibrosis Transmembrane Conductance Regulator (CFTR).

* * * * *